United States Patent
Hameed et al.

(10) Patent No.: US 12,008,758 B2
(45) Date of Patent: *Jun. 11, 2024

(54) DETECTION OF POLYPS

(71) Applicant: PSIP LLC, Manchester, NH (US)

(72) Inventors: Salmaan Hameed, San Jose, CA (US); Giau Nguyen, San Jose, CA (US)

(73) Assignee: PSIP LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/952,234

(22) Filed: Sep. 24, 2022

(65) Prior Publication Data

US 2023/0334666 A1     Oct. 19, 2023

Related U.S. Application Data

(63) Continuation of application No. 16/189,765, filed on Nov. 13, 2018, now Pat. No. 11,455,726, which is a
(Continued)

(51) Int. Cl.
*G06T 7/00* (2017.01)
*A61B 1/00* (2006.01)
(Continued)

(52) U.S. Cl.
CPC ...... *G06T 7/0014* (2013.01); *A61B 1/000094* (2022.02); *A61B 1/000096* (2022.02); *A61B 1/0014* (2013.01); *A61B 1/00177* (2013.01); *A61B 1/00181* (2013.01); *G01B 11/03* (2013.01); *G01B 11/30* (2013.01); *G06V 10/454* (2022.01); *G06V 10/50* (2022.01); *G06V 10/764* (2022.01); *G06V 10/82* (2022.01);
(Continued)

(58) Field of Classification Search
CPC ........ G06T 7/0014; G06T 2207/10068; G06T 2207/30032; A61B 1/000094; A61B 1/000096; A61B 1/0014; A61B 1/00177; A61B 1/00181; A61B 1/00101; G01B 11/03; G01B 11/30; G06V 10/454; G06V 10/50; G06V 2201/032; G06V 2201/034; G06F 18/2414
USPC ....................................................... 382/128
See application file for complete search history.

(56) References Cited

U.S. PATENT DOCUMENTS 8,023,710 B2 * 9/2011 Summers ............. A61B 5/7267
                                                          382/128
2003/0158470 A1 * 8/2003 Wolters ................. A61B 1/043
                                                          600/317
(Continued)

FOREIGN PATENT DOCUMENTS

EP     1374168 A2 * 1/2004     ........... G06K 9/3233
GB     2367966 A  * 4/2002     ........... G06K 9/3233
(Continued)

*Primary Examiner* — Mahendra R Patel
(74) *Attorney, Agent, or Firm* — David E. Boundy; Potomac Law Group PLLC

(57) ABSTRACT

Identifying polyps or lesions in a colon. In some variations, computer-implemented methods for polyp detection may be used in conjunction with an endoscope system to analyze the images captured by the endoscopic system, identify any polyps and/or lesions in a visual scene captured by the endoscopic system, and provide an indication to the practitioner that a polyp and/or lesion has been detected.

32 Claims, 13 Drawing Sheets

Related U.S. Application Data continuation of application No. PCT/US2017/033675, filed on May 19, 2017.

(60) Provisional application No. 62/339,019, filed on May 19, 2016.

(51) Int. Cl.
  G01B 11/03 (2006.01)
  G01B 11/30 (2006.01)
  G06F 18/2413 (2023.01)
  G06V 10/44 (2022.01)
  G06V 10/50 (2022.01)
  G06V 10/764 (2022.01)
  G06V 10/82 (2022.01)

(52) U.S. Cl.
  CPC ...... *A61B 1/00101* (2013.01); *G06F 18/2414* (2023.01); *G06T 2207/10068* (2013.01); *G06T 2207/30032* (2013.01); *G06V 2201/032* (2022.01); *G06V 2201/034* (2022.01)

(56) References Cited

U.S. PATENT DOCUMENTS

| | | | | |
|---|---|---|---|---|
| 2003/0191368 A1* | 10/2003 | Wang | ............... | A61B 1/043 600/476 |
| 2007/0167749 A1* | 7/2007 | Yarnall | ............... | G01T 1/2985 600/431 |
| 2008/0058593 A1* | 3/2008 | Gu | ............... | G06T 5/40 600/109 |
| 2010/0158330 A1* | 6/2010 | Guissin | ............... | G06T 7/90 382/128 |
| 2010/0246912 A1* | 9/2010 | Periaswamy | ............... | G06F 18/00 382/128 |
| 2011/0013556 A1* | 1/2011 | Molnar | ............... | G06T 1/00 370/328 |
| 2012/0230559 A1* | 9/2012 | Itai | ............... | G06T 7/0012 382/128 |
| 2013/0121546 A1* | 5/2013 | Guissin | ............... | G06T 7/0012 382/128 |
| 2015/0065850 A1* | 3/2015 | Jia | ............... | G06T 7/0012 600/408 |
| 2015/0313445 A1* | 11/2015 | Davidson | ............... | G06T 3/4038 600/109 |
| 2016/0078625 A1* | 3/2016 | Tajbakhsh | ............... | G06T 7/0012 382/128 |
| 2016/0217573 A1* | 7/2016 | Lian | ............... | G06T 5/20 |
| 2017/0055814 A1* | 3/2017 | Wang | ............... | G06T 7/0012 |
| 2017/0164928 A1* | 6/2017 | Oh | ............... | A61B 8/483 |
| 2017/0344900 A1* | 11/2017 | Alzahrani | ............... | G06F 16/435 |
| 2018/0049643 A1* | 2/2018 | Balog | ............... | H01J 49/0004 |
| 2018/0075599 A1* | 3/2018 | Tajbakhsh | ............... | G06T 1/0007 |

FOREIGN PATENT DOCUMENTS

| | | | | |
|---|---|---|---|---|
| WO | WO-03034176 A2 * | 4/2003 | ............ | G06T 7/0012 |
| WO | WO-2007105517 A1 * | 9/2007 | ............ | G06K 9/4609 |
| WO | WO-2011151821 A1 * | 12/2011 | ............ | G06T 7/0012 |
| WO | WO-2014155778 A1 * | 10/2014 | ......... | A61B 1/00009 |
| WO | WO-2015168066 A1 * | 11/2015 | ......... | A61B 1/00006 |

* cited by examiner

DETECTION OF POLYPS

This application is a continuation of U.S. application Ser. No. 16/189,765, filed Nov. 13, 2018, titled Methods for Polyp Detection, now issued as U.S. Pat. No. 11,455,726; which is a continuation of International Application Serial No. PCT/US2017/033675, filed May 19, 2017; which claims benefit of U.S. Provisional Application Ser. No. 62/339,019, filed May 19, 2016. These applications are incorporated by reference.

BACKGROUND

Colonoscopies are medical procedures that utilize a viewing instrument to examine the interior surface of a colon, which may be used to identify anatomical abnormalities that may be precursors to colorectal cancer or other intestinal disorders. The American Cancer Society recommends colonoscopies every 10 years for men and women of average colorectal cancer risk, starting at age 50, but earlier and/or more frequent colonoscopies are recommend for patients at higher risk, including people with a history of prior polyps or inflammatory bowel disease, or a family history of certain genetic colonic diseases. During a colonoscopy, a practitioner scans the interior surface of a colon using an endoscope (i.e., a colonoscope) to visually identify lesions, erosions, polyps, atypical surface textures or coloration, grooves and/or granularities in the mucosal surface of the colon. Typically, the patient will ingest a colon preparation solution procedure prior to the colonoscopy to clear out the contents of their colon. This reduces the amount of stool in the colon so that structures and/or textures on the surface of the colon can be readily scanned, thereby facilitating the identification of polyps and/or lesions.

Because the interior surface of the colon has many curves and folds, and the quality of the bowel preparation varies, it may be difficult to identify polyps and a practitioner may overlook a polyp or lesion. Furthermore, it is in the interest of both the practitioner and the patient for the colonoscopy to proceed in an expedient manner. Accordingly, improvements to the accuracy of identifying polyps and/or lesions (e.g., reducing the rate of false positive or false negative results) and efficiency of colonoscopies are desirable.

SUMMARY

Disclosed herein are methods for identifying polyps or lesions in a colon. In some variations, computer-implemented methods for polyp detection may be used in conjunction with an endoscope system to analyze the images captured by the endoscopic system, identify any polyps and/or lesions in a visual scene captured by the endoscopic system, and provide an indication to the practitioner that a polyp and/or lesion has been detected. Some methods may comprise analyzing a one or more static images or video to identify regions with abnormal structure or patterns, determining the likelihood or probability that such region may have a polyp and/or lesion, and prompting the practitioner to visually inspect that region more closely. Computer-implemented methods of polyp detection may be performed during at least a portion of the colonoscopy procedure, in real-time (e.g., in about 30 ms or less). In some variations, an endoscopic system may comprise a plurality of imaging devices, for example, one or more front-facing imaging devices, one or more side-facing imaging devices, and/or one or more rear-facing imaging devices. Any of the polyp detection methods described herein may be used to analyze the image data from any one or more of the plurality of imaging devices and to provide a notification to the practitioner when a polyp is identified. In some variations, the notification may include location information (optionally, with navigation instructions to the polyp) and/or anatomical information about the identified polyp (optionally, an image of the colon wall with the boundaries of the polyp outlined).

One example of a method for detecting polyps may comprise acquiring an image from an imaging device located at a distal portion of an endoscope, identifying surface peaks in the image, identifying clusters of surface peaks based on a predetermined threshold separation distance, selecting a surface peak from each identified cluster, defining a pixel region around each of the selected surface peaks, comparing image features in each of said defined pixel regions with image features of a plurality of images containing polyps and image features of a plurality of images that do not contain polyps, and if an image feature in a defined pixel region matches image features of a plurality of images containing polyps, generating a notification that a polyp has been detected. In some variations, the step of comparing image features may comprise computing a histogram of oriented gradients (HOG) to extract surface peaks from the plurality of images containing polyps (HOG-PI), computing a histogram of oriented gradients (HOG) to extract surface peaks from the plurality of images that do not contain polyps (HOG-NPI), computing a histogram of oriented gradients (HOG) of the image enclosed by a defined rectangle (HOG-ROI), comparing HOG-ROI with HOG-PI and HOG-NPI, and if the similarity between HOG-ROI to HOG-PI exceeds a preselected threshold, determining that a polyp is detected. In some variations, the preselected similarity threshold may be at least 50% similarity. In some variations, generating a notification may comprise transmitting an image of the detected polyp to a display and optionally providing an arrow configured to indicate the location of the polyp with respect to a distal end of the endoscope.

A method for polyp detection may comprise acquiring an image from an imaging module located at a distal portion of an endoscope, identifying surface peaks in the image, identifying clusters of surface peaks based on a predetermined threshold separation distance, defining a pixel region around each of the selected surface peaks, comparing an image feature in each of the defined pixel regions with a corresponding image feature of a plurality of images containing polyps and a corresponding image feature of a plurality of images that do not contain polyps, and if the image feature in a defined pixel region matches the corresponding image feature of a plurality of images containing polyps, generating a notification that a polyp has been detected. Comparing the image feature may comprise computing a histogram of oriented gradients to extract surface peaks from the plurality of images containing polyps (HOG-PI), computing a histogram of oriented gradients to extract surface peaks from the plurality of images that do not contain polyps (HOG-NPI), computing a histogram of oriented gradients of the image enclosed by a defined rectangle (HOG-ROI), and if the similarity between HOG-ROI to HOG-PI exceeds a preselected similarity threshold, determining that a polyp is detected. The preselected similarity threshold may be at least 50% similarity. In some variations, the image feature may comprise a curvature of a high-contrast edge, and/or spatial frequency. Comparing image features in each of the defined pixel regions may comprise applying a convolutional neural network (CNN) to the pixel regions, and calculating a numerical output based on the CNN for each pixel region that indicates whether the pixel region contains a polyp. Comparing an image feature may comprise applying a convolutional neural network (CNN) to each pixel region. Applying a CNN may comprise generating a first filtered pixel region by filtering the pixel region with a first filter to identify one or more polyp-like features, generating a second filtered pixel region by filtering the first filtered pixel region with a second filter to identify one or more non-polyp features, generating a notification that a polyp has been detected if a second filtered pixel region of the defined pixel regions has been identified to have a higher incidence of polyp-like features than non-polyp features.

The plurality of images containing polyps and the plurality of images that do not contain polyps may be stored on a remote memory or server. Generating a notification may comprise transmitting an image of the detected polyp to a display and may optionally comprise providing an arrow configured to indicate the location of the polyp with respect to a distal end of the endoscope. In some variations, the imaging module may comprise a first side-facing imaging device and a second side-facing imaging device, and acquiring an image may comprise acquiring a first image from the first side-facing imaging device and a second image from the second side-facing imaging device. Image features in each of said defined pixel regions may be compared by applying a first CNN to pixel regions of the first image and applying a second CNN to pixel regions of the second image. The endoscope may comprise a front-facing imaging device, and acquiring an image may comprise acquiring a third image from the front-facing imaging device and comparing image features may comprise applying a third CNN to pixel regions of the third image.

A method for polyp detection may comprise applying a convolutional neural network (CNN) to an image of the colon. Applying a CNN to an image may comprise selecting a first set of sub-regions of the image by applying a first convolution stage of the CNN to the image, the first convolution stage comprising a first polyp-positive filter that identifies sub-regions of the image containing a polyp-like feature, selecting a second set of sub-regions from the first set of sub-regions by applying a second convolution stage of the CNN to the first set of sub-regions, where the second convolution stage may comprise a second polyp-positive filter that identifies the incidence of a polyp-like feature in a sub-region and a polyp-negative filter that identifies the incidence of a non-polyp feature in a sub-region, selecting a third set of sub-regions by identifying sub-regions in the second set of sub-regions where a ratio of the incidence of the polyp-like feature to the incidence of the non-polyp feature exceeds a pre-determined threshold, and generating an output that indicates the presence of a polyp within the image if the number of sub-regions in the third set of sub-regions meets or exceeds a pre-determined count threshold. Generating an output may comprise generating an output if the ratio of the number of sub-regions in the third set to the number of sub-regions in the second set meets or exceeds a pre-determined ratio threshold. The polyp-like feature may comprise a high-contrast edge with a curve with a radius-of-curvature from about 2 mm to about 7 mm, and/or may comprise a pixel having a local maximum intensity that is located within an inner curve of the high-contrast edge. Alternatively or additionally, the polyp-like feature may comprise surface peaks identified by calculating a histogram of oriented gradients of a plurality of polyp-positive colon images (HOG-PI). The non-polyp feature may comprise low-contrast edges with a spatial frequency that exceeds a pre-determined spatial frequency threshold, and/or surface peaks identified by calculating a histogram of oriented gradients of a plurality of polyp-negative colon images (HOG-NPI). The first polyp-positive filter may be the same as or different from, the second polyp-positive filter. The first convolution stage and/or the second convolution stage may comprise a low-pass filter. The CNN may be a first CNN, and a polyp detection method may optionally comprise applying a second CNN to the image of the colon, where the second CNN may comprise a first convolution stage having a third polyp-positive filter and a second convolution stage having a fourth polyp-positive filter and a second polyp-negative filter. The polyp-like feature may be a first polyp-like feature and the third polyp-positive filter may identify sub-regions of the image containing a second polyp-like feature different from the first polyp-like feature. The image may be a first image acquired by a first imaging device, and the CNN may be a first CNN, and the method may optionally comprise applying a second CNN to a second image of the colon acquired by a second imaging device. In some variations, the first imaging device may be a first side-viewing device and the second imaging device may be a second side-viewing device.

Also disclosed herein is a detachable imaging device comprising an imaging module and a clip attached to the imaging module. The imaging module may comprise a housing having a front face, a back face, a first side-facing imaging element and a second side-facing imaging element and the clip may be configured to be releasably disposed over a distal portion of an endoscope. The clip may comprise a first engagement portion having a front facing edge, a back facing edge, and a bottom edge, and a second engagement portion having a front facing edge, a back facing edge, and a bottom edge. A space between the first and second engagement portions may define an endoscope attachment region and the back facing edges of the first and second engagement portions each have an atraumatic protrusion having a rounded contour along the lengths of the back facing edges. The bottom edges of the first and second engagement portions may each have an atraumatic protrusion having a rounded contour along the lengths of the bottom edges. Optionally, the atraumatic protrusions of each of the bottom edges may comprise an inward-facing lip that extends into the endoscope attachment region.

The above advantages and features are of representative embodiments only, and are presented only to assist in understanding the invention. It should be understood that they are not to be considered limitations on the invention as defined by the claims. Additional features and advantages of embodiments of the invention will become apparent in the following description, from the drawings, and from the claims.

DESCRIPTION

Figure 1A:
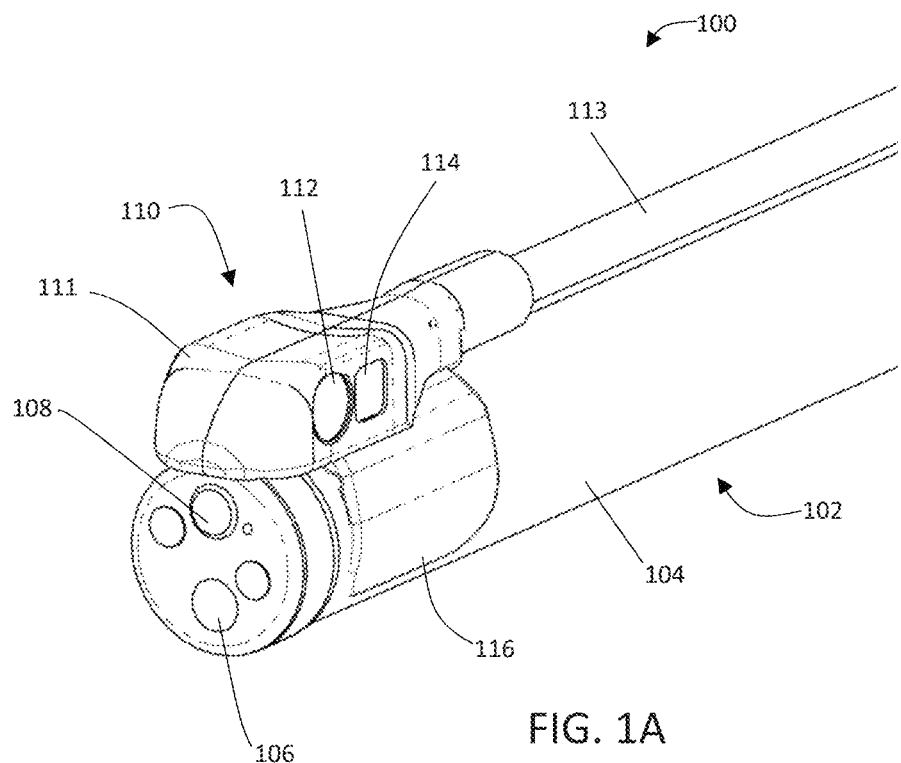
FIG. 1A depicts one variation of an endoscope system.

Described herein are methods for polyp detection. The methods may be computer-implemented methods comprising computer executable instructions stored in the memory of a controller or processor.

The methods for polyp detection disclosed herein may be used in conjunction with a variety of endoscopes adapted for scanning the interior surface of a colon (e.g., colonoscopes). For example, methods for polyp detection may be used with endoscope systems comprising a single imaging device that has a forward-facing view (e.g., a field of view that extends from the distal end of the elongate body of an endoscope), and may also be used with endoscope systems comprising a plurality of imaging devices with various overlapping and/or non-overlapping views. In some variations, an endoscope or colonoscope system may comprise an elongate body having a proximal portion, a distal portion, and side walls extending between the proximal and distal portions, a first imaging device located at a distal portion of the elongate body and having a field-of-view that extends from the distal end of the elongate body (e.g., a forward view, front-facing), and one or more imaging devices located along the sidewalls of the elongate body. The one or more imaging devices located on the sidewall of the elongate body may have field-of-views that extend from the side of the elongate body (e.g., side views, rearward views). For example, an endoscope or colonoscope system may comprise a first side-mounted (e.g., side-facing) imaging device having a first field-of-view that extends from a first sidewall of the elongate body in a first direction and a second side-mounted (e.g., side-facing) imaging device having a second field-of-view that extends from a second sidewall of the elongate body in a second direction that is different from the first direction. Some variations may optionally comprise a side-mounted imaging device that may have a field-of-view that extends rearwardly relative to the field-of-view of a front-facing imaging device, and/or a side-mounted imaging device that may have a field-of-view that extends above or below the elongate body. The viewing angle of the one or more side-mounted imaging devices relative to the longitudinal axis of the elongate body may be from about 0 degrees (i.e., parallel or coaxial with the longitudinal axis of the elongate body) to about 179 degrees, for example, about 90 degrees, about 75 degrees, about 120 degrees, about 135 degrees, etc. The field-of-views of the front-facing and the one or more side-mounted imaging devices may or may not overlap. In some variations, at least a portion of the field-of-views of the front-facing and the one or more side-mounted imaging devices may overlap. Field-of-views having some degree of overlap may facilitate the combination or stitching of multiple images from multiple imaging devices together to simulate a continuous view. In some variations, the continuous view may be a panoramic view having a cumulative field-of-view of at least about 120 degrees, at least about 135 degrees, at least about 150 degrees or more. In some variations, the one or more side-mounted imaging devices may be integral with the elongate body, while in other variations, the one or more side-mounted imaging devices may be releasably attached to the elongate body.

One example of an endoscope (e.g., colonoscope) system comprising an endoscope with a front-facing imaging device and one or more detachable side-facing imaging devices is depicted in FIG. 1A. Endoscope system 100 may comprise an endoscope 102 comprising an elongate body 104 and a front-facing imaging device 106 located at the distal end of the elongate body, and a detachable imaging module 110 comprising a first side-facing imaging device 112 and a second side-facing imaging device (not shown; located on the side opposite to the first side-facing imaging device). The detachable imaging module 110 may comprise a clip or clamp 116 configured to attach to the sidewalls of a distal portion or length of the elongate body 104. The clip or clamp may attach to the elongate body such that it spans a substantial portion of the circumference of the elongate body, and in some cases, may span the entire circumference of the elongate body or nearly the entire circumference of the elongate body. For example, the two sides of the clip or clamp may span more than about 50% of the circumference, or more than about 60% of the circumference, or more than about 70% of the circumference, or more than about 80% of the circumference, or more than about 90% of the circumference, or more than about 95% of the circumference, etc. Alternatively or additionally, the detachable imaging module may comprise a sleeve (e.g., an elastic or deflectable sleeve) that it encloses the entire circumference of the outer surface of the elongate body. The endoscope 102 may optionally comprise a first light emitter 108 located on the distal end of the elongate body and configured to provide illumination for the field-of-view of the front-facing imaging device 106. The detachable imaging module 110 may also comprise a second light emitter 114 located adjacent to the first side-facing imaging device 112 and configured to provide illumination for the field-of-view of the side-facing imaging device. A third light emitter (not shown) may be located adjacent to the second side-facing imaging device. In this variation, the axes of the field-of-view of the first and second side-facing imaging devices may be tangential to the surface of the elongate body 104 and/or perpendicular to the longitudinal axis of the elongate body, while the axis of the field-of-view of the front-facing imaging device may be approximately parallel to the longitudinal axis of the elongate body.

Figure 1B:
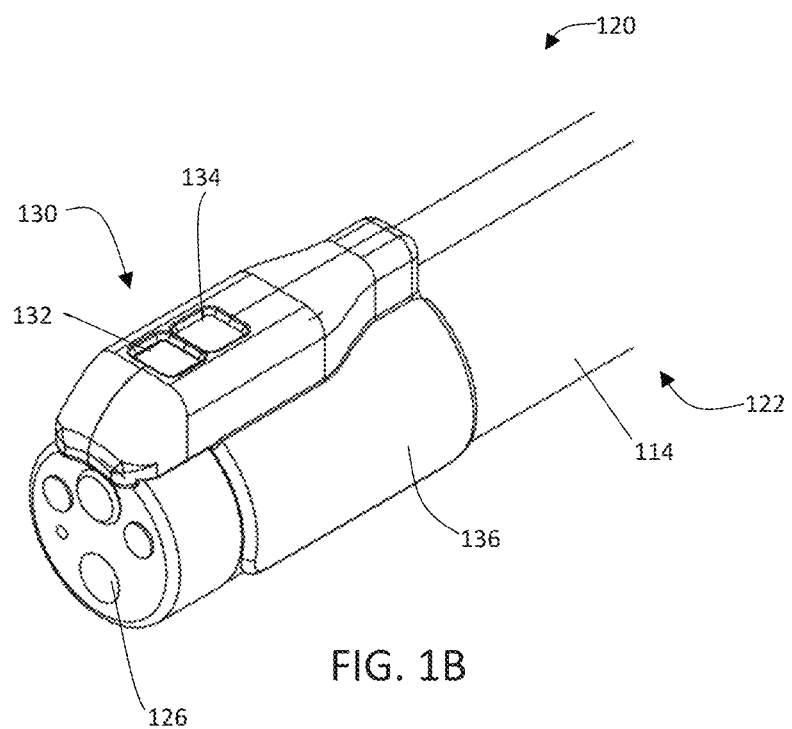
FIG. 1B depicts another variation of an endoscope system.

The light-emitters of the detachable imaging module may comprise one or more light sources, such as light-emitting diodes (LEDs), located within a housing 111 of the imaging module. Alternatively or additionally, the light-emitters of the detachable imaging module may comprise one or more optical fibers connected to a light source located outside of the housing 111. For example, the light source may be located at a proximal portion of the endoscope system, and the optical output may be channeled through the one or more optical fibers to a distal portion of the endoscope system to the imaging module. The ends of the optical fibers may be located at an opening in the housing to provide illumination for the field-of-view for the side-facing imaging device. The optical fibers (along with any other control, power and/or data wires) may be enclosed within a cable conduit 113 that is located along the outside of the elongate body 104 and connected to the housing 111 of the detachable imaging module. FIG. 1B depicts another variation of an endoscope system 120 comprising an endoscope 122 comprising an elongate body 124 and a first front-facing imaging device 126, similar to that described above with respect to FIG. 1A. The endoscope system 120 may also comprise a detachable imaging module 130 comprising a top-viewing imaging device 132 that has a field-of-view that has a view axis that is perpendicular to both the surface elongate body 124 and the longitudinal axis of the elongate body. Optionally, the detachable imaging module 130 may also comprise a light emitter 134 located adjacent to the top-facing imaging device 132 and configured to illuminate the field-of-view of the top-facing imaging device 132. The detachable imaging module 120 may further comprise a clip or clamp 136 that attaches to the sidewall at the distal portion of the elongate body 114.

The shape and contours of the housing, along with the shape and contours of the clip/clamp of any of the detachable imaging modules described herein may comprise one or more atraumatic features. For example, the housing and the clip/clamp may have rounded edges and/or tapers to help promote smooth motion through the colon, without engaging or catching the curves and folds of the interior surface of the colon. The front face (e.g. distal face) and/or the back face (e.g., proximal face) of the housing of a detachable imaging module may comprise a rounded tapered contour where the front portion of the housing is narrower than the middle portion of the housing. Optionally, the contours and edges of the clip/clamp may also have rounded surfaces and/or tapers to help prevent engaging or catching the colon wall. Some variations may also have similar atraumatic contours on the back face of the housing. FIGS. 1D-1E depict a detachable imaging module 140 comprising a housing 141, a first side-facing imaging device 142 and a second side-facing imaging device (not shown; located on the side opposite to the first side-facing imaging device), a first light-emitter 144 and a second light-emitter (not shown; located on the side opposite to the first light-emitter). The detachable imaging module 140 may also comprise a clip/clamp or sleeve 146 coupled to the housing 141 to atraumatically secure the imaging module to an endoscope or colonoscope. The clip 146 may comprise a first engagement portion 152 and a second engagement portion 154, and each of the engagement portions may have curves that approximate the curvature of the outer surface of an endoscope. The engagement portions may be flexible and resilient so that the gap between them may be enlarged to insert an endoscope therebetween and then once the endoscope is seated between the engagement portions, they may be inwardly biased to attach over the endoscope. The engagement portions 152, 154 may span over the majority of the circumference of the endoscope in order to secure the imaging module thereto. In some variations, the engagement portions may span over at least about 80% (e.g., about 85% or more, about 95% or more) of the total circumference of the outer surface of the endoscope, which may help provide a smoother profile with fewer edges or protrusions that may unintentionally engage the interior surface of the colon. Spanning a larger portion of the circumference may also facilitate secure engagement with the elongate body of the endoscope.

The side edges 153 (i.e., the front facing side edges and/or the back facing side edges) and bottom edges 155 of the engagement portions may have rounded or tapered atraumatic contours, as well as enlarged or flattened contours to help distribute any forces over a larger area of tissue. This may help to reduce the incidence of localized regions of high forces that may result in pinching or engagement of any folds or curves in the colon. For example, the bottom edges 155 of the clip/clamp 146 of FIGS. 1D and 1E may have enlarged, rounded contours which may help distribute any inward clamping forces across a larger surface, and/or allow for an even distribution of lateral forces as the endoscope system is moved within the lumen of the colon (e.g., across the interior surface of the colon). The enlarged, rounded contours 158 may include a lip or inward protrusion 157 located on the inner portion of the bottom edges of the engagement portions, which may help engage the elongate body of an endoscope between the engagement portions 152, 154. FIGS. 1F-1G depicts a variation of a detachable imaging module 160 that may be substantially similar to the other detachable imaging modules described above. The imaging module 160 may comprise a clip or clamp 166 having first and second engagement portions 162, 164, each comprising side edges and bottom edges 175. The bottom edges 175 may also have enlarged rounded contours 168, but unlike the contours 158 depicted in FIG. 1E which have a lip or inward protrusions (i.e., into the space between the two engagement portions) and outward protrusions, the enlarged rounded contours 168 have outward protrusions but no lip or inward protrusions. Alternatively or additionally, bottom edges may be tapered so that the outermost portion of the engagement portion edge region is thinner than an inner portion of the edge region. The side edges on the front-facing side and/or the back-facing side may comprise any one or combination of the curves, contours, tapers described above. For example, a back facing side edge of a detachable imaging module clip may comprise one or more of the atraumatic curves, contours and/or tapers described above to help facilitate the withdrawal of a colonoscope with the detachable imaging module in the colon. In the event that the detachable imaging module is separated from the colonoscope while within the colon (e.g., during a colonoscopy), the atraumatic curves, contours and/or tapers on the imaging module may help reduce trauma and/or tissue damage to the colon wall as the imaging module is withdrawn from the colon.

Figure 1C:
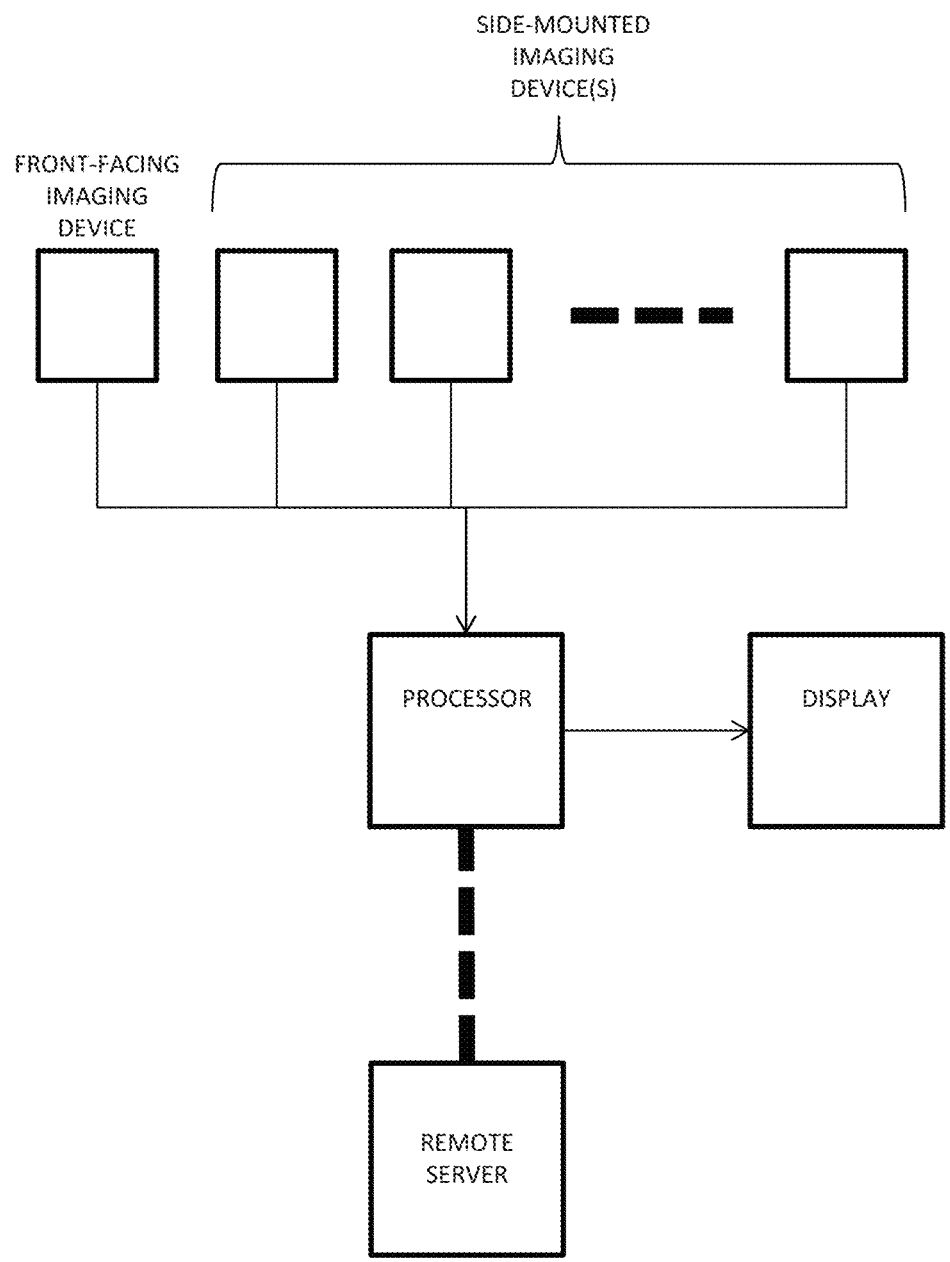
FIG. 1C is a schematic representation of one variation of an imaging system and corresponding processor, display, and remote server that may support any of the endoscope systems described herein.
Figure 1D:
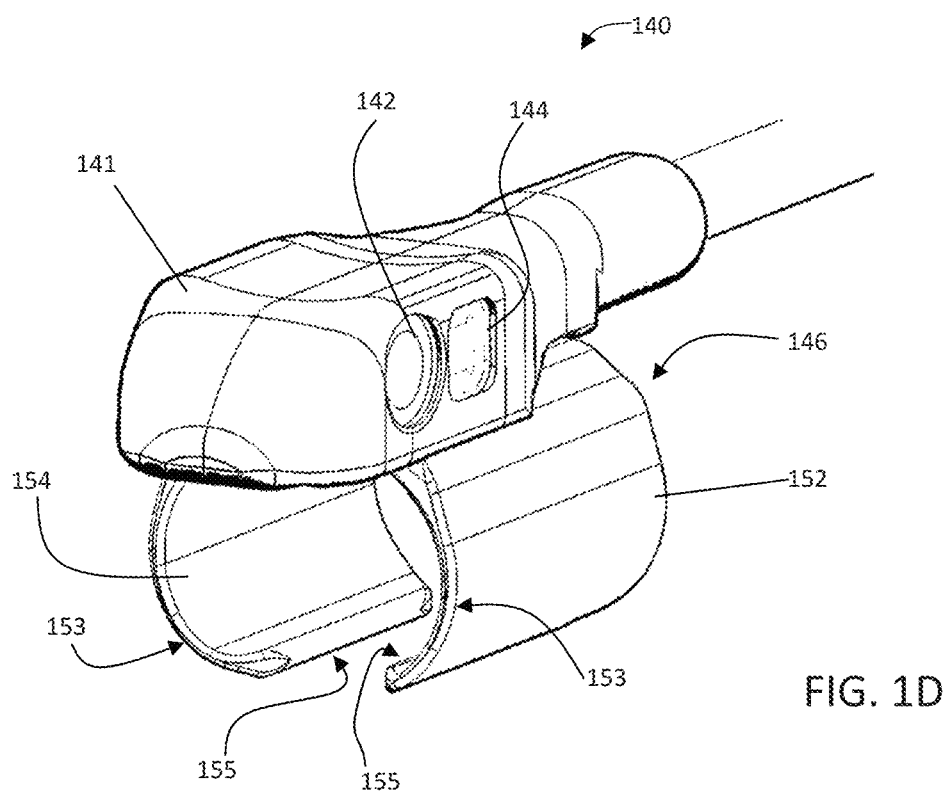
FIG. 1D depicts a perspective view of one variation of a detachable imaging module.
Figure 1E:
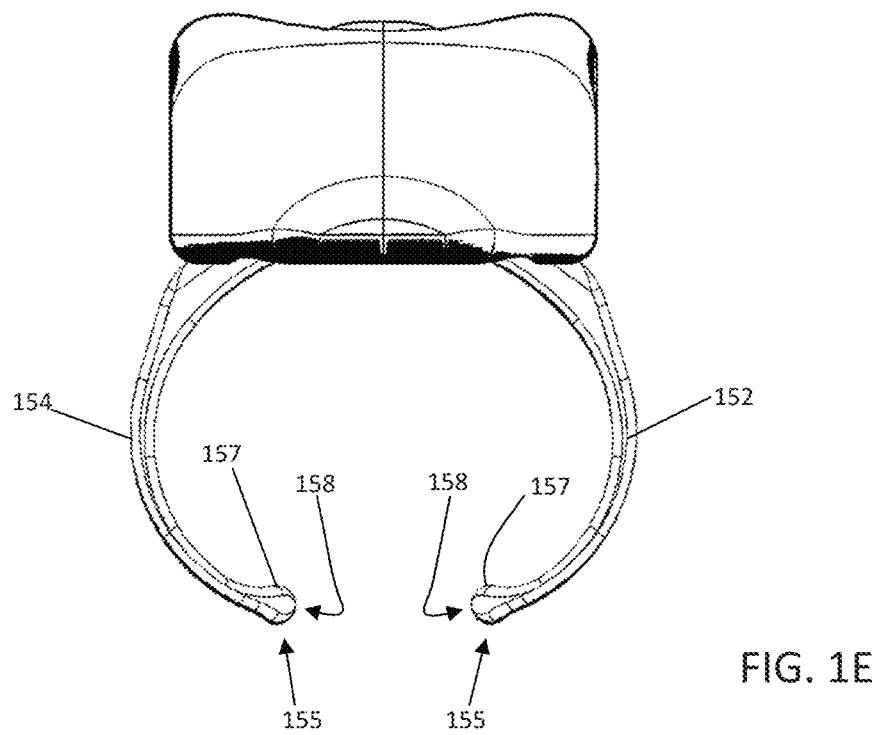
FIG. 1E depicts a front view of the detachable imaging module of FIG. 1D.
Figure 1F:
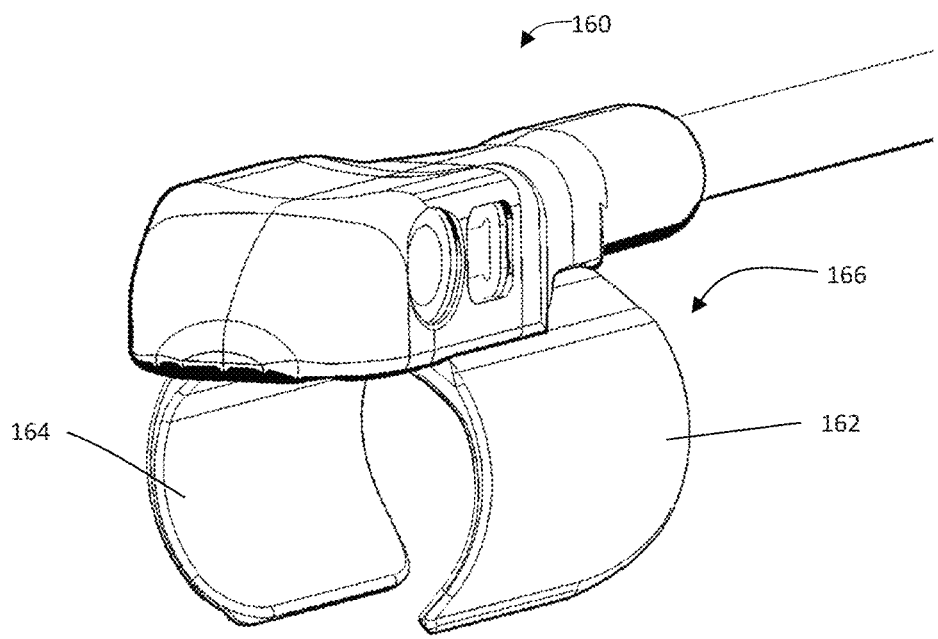
FIG. 1F depicts a perspective view of one variation of a detachable imaging module.
Figure 1G:
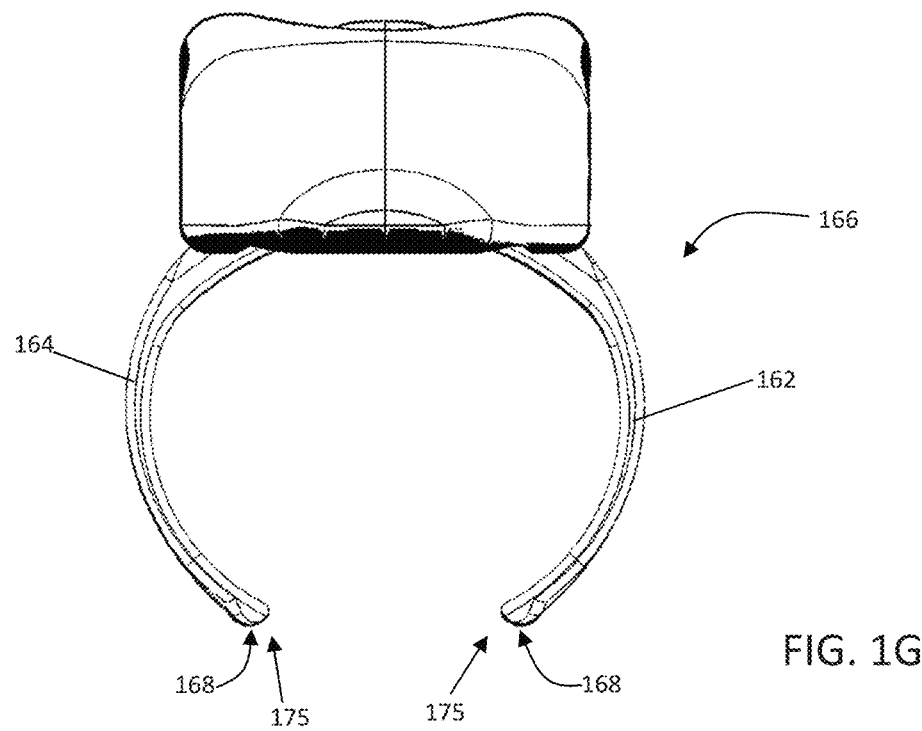
FIG. 1G depicts a front view of the detachable imaging module of FIG. 1F.

The endoscope systems of FIGS. 1A-1B and 1D-1G may further comprise a processor or controller in communication with the front-facing imaging device and/or the one or more side-mounted imaging devices, and a display in communication with the processor, as depicted in FIG. 1C. Optionally, the processor may be connected to a remote server via wired or wireless connections. Examples of data transferred from the local processor or controller to the remote server may include, but are not limited to, images of the colon, images of polyps or lesions, colon images that have been classified as containing a polyp (polyp-positive images), colon images that have been classified as not containing a polyp (polyp-negative images), and patient-specific data, such as quality of the bowl preparation, date and time of a colonoscopy procedure, practitioner notes regarding the procedure and the like. Examples of data transferred from the remote server to the processor may include sets of polyp image data collected over one or more populations of patients, sets of colon images that do not have polyps or lesions, patient-specific data and the like. Additional variations and descriptions of endoscope systems in which the polyp detection methods described herein may be applied are described in co-pending U.S. Patent Application Pub. No. 2014/0343358, filed May 16, 2014. While the imaging devices depicted and described above are detachable from the elongate body of an endoscope or colonoscope, it should be understood that the optical components of the detachable imaging devices may also be integrated within and/or fixedly attached to the elongate body.

The imaging devices (front-facing and/or side-facing) may acquire still images or may acquire a stream of images (e.g., video) that may be transmitted to the processor for analysis, for example, using polyp detection methods. Polyp detection methods may be stored in a memory of a controller or processor as computer-executable instructions, for example. In other variations, polyp detection methods may be implemented in computer hardware, for example, in the form of logic gates (e.g., in a FPGA or ASIC). In the variations described herein, the images from the side-mounted imaging devices are analyzed by the processor or controller using polyp detection methods, however, it should be understood that alternatively or additionally, the images from the front-facing imaging device may be analyzed using similar polyp detection methods.

Figure 2A:
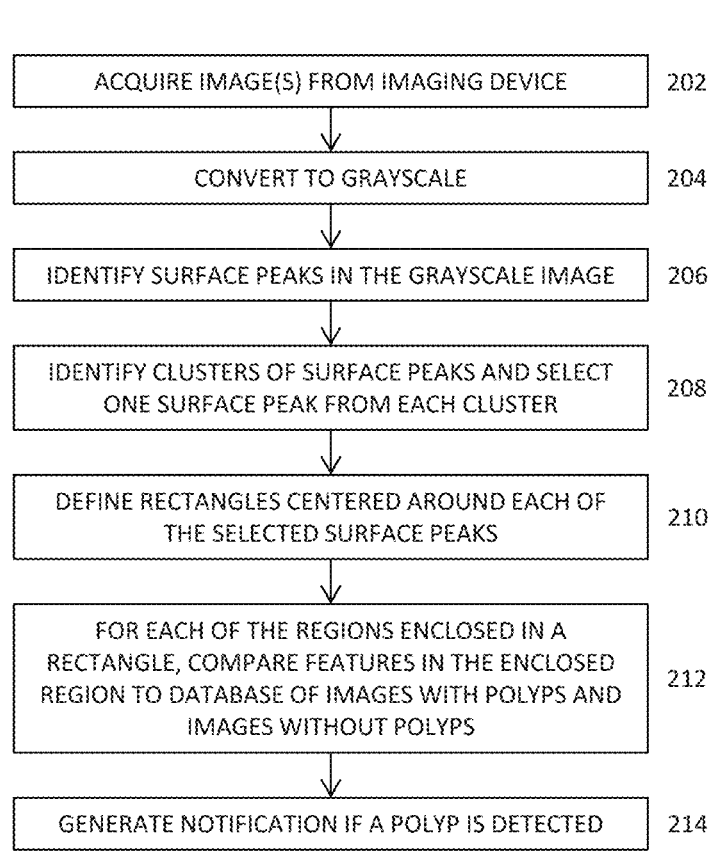
FIG. 2A is a flowchart depiction one variation of a method for polyp detection.

One variation of a polyp detection method is depicted in FIG. 2A. Method 200 may comprise acquiring 202 an image from an imaging device. The image may be acquired in real-time, or may an image acquired in a previous imaging session and stored in machine-readable memory. The processor may optionally convert 204 the images to grayscale (i.e., depending on whether the imaging device acquired the image(s) in color or in black and white). Method 200 may comprise identifying surface peaks 206 in the grayscale image. Surface peaks may represent surface regions or points that are located at the top surface or the bottom surface of a fold, as identified by local intensity extremums (e.g., minimums or maximums, respectively) in the image. For example, a surface peak that is located at the bottom of a fold may be further from the imaging device(s) than a surface peak that is located at the top of a fold, and the difference in distance may be determined by calculating the intensity difference between the identified surface peaks. A surface peak that is located at the top of a fold may be brighter (e.g., more intense) than a surface peak that located at the bottom of the fold, and the intensity difference may indicate the distance between the two peaks. Variations of methods that may be used to identify surface peaks may include various blob detection methods such as MSER (maximally stable extremal regions). A blob detection method may comprise performing luminance or intensity thresholding of the image (e.g., sweeping the luminance or intensity threshold from low/black to high/white), identifying "extremal regions" by extracting connected components, finding a threshold where the extremal regions are stable, and storing the extremal regions as a set of surface peaks. For example, a MSER method may comprise generating a sequence of images from a raw image, where each image is derived from the raw image by applying varying intensity thresholds. In some variations, a thresholded image may be derived from a raw image by assigning all pixels below (or above) a first threshold to be white (e.g., maximum intensity) and pixels at or above (or below) the first threshold to be black (e.g., minimum intensity). A second thresholded image may be generated in a similar fashion, but instead using a second threshold that is different from the first threshold, and so on (e.g., monotonically increasing or decreasing the intensity threshold). A MSER method may further comprise identifying extremal regions within the raw image by selecting one or more thresholded images that have groups of white pixels that stay nearly the same through a range of thresholds. These extremal regions may correspond to surface peaks.

Alternatively or additionally, surface peaks that are located in close proximity to each other may be used to approximate the curvature of the interior surface of the colon. For example, the separation between a surface peak at the top of a fold and a surface peak at the bottom of a fold may indicate whether the surface curvature is a fold or a polyp. For example, if the separation between surface peaks is relatively little (e.g., below a pre-determined separation threshold) and the distance between the peaks (e.g., as calculated based on intensity) is relatively high (e.g., above a pre-determined distance threshold), it may be that the slope of the surface curve is relatively high. A sharper surface curve, alone or in combination with other polyp-like features, may indicate the presence of a polyp. If the separation between surface peaks is relatively high (e.g., above a pre-determined separation threshold) and the distance between the peaks (e.g., as calculated based on intensity) is relatively low (e.g., below a pre-determined distance threshold), it may be that the slope of the surface curve is relatively low. A low-slope surface curve may indicate that there is a fold or undulation in the surface, but no polyp.

Figure 3A:
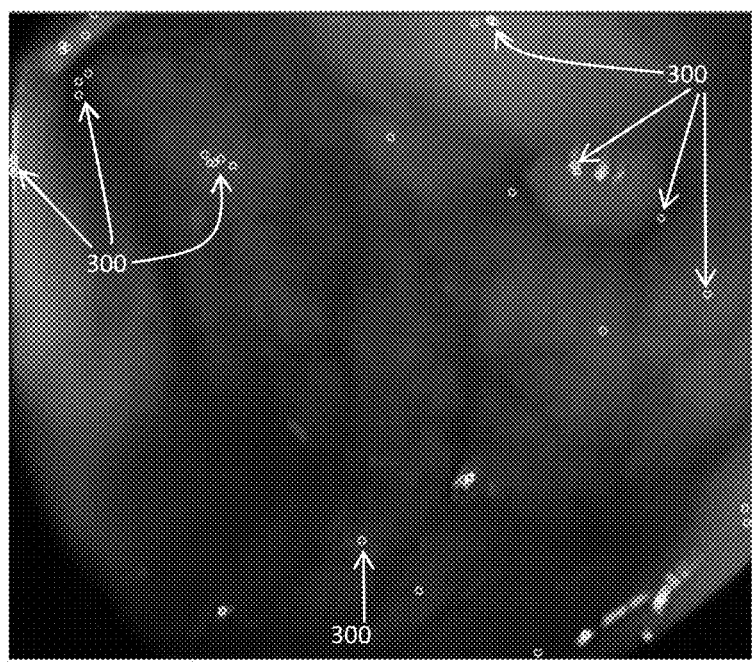
FIGS. 3A-3D depict an example of an image that has been analyzed and processed in accordance with the method of FIG. 2A.
Figure 3B:
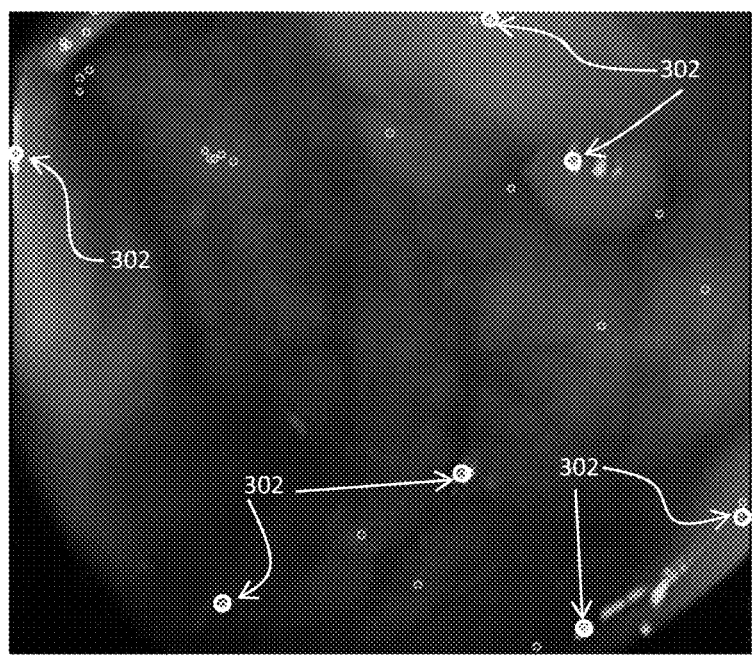

FIGS. 3A-3D depict an example of an image of an interior surface of a colon that contains a polyp, and are annotated to indicate the effect of the method steps depicted in FIG. 2A. FIG. 3A depicts an image where the plurality of circles 300 indicate the surface peaks identified as a result of step 206. Method 200 may further comprise identifying clusters 208 of surface peaks and selecting one surface peak from each cluster. A cluster of surface peaks may be defined as any group of surface peaks that are no more than a selected or predetermined distance apart from each other. For example, the selected or predetermined distance value may be from about 0.1 mm to about 20 mm, e.g., about 16 mm, about 17 mm, etc. The selected or predetermined distance value may also be defined in terms of image pixels, and may be from about 1 pixel to about 200 pixels, e.g., about 50 pixels, about 100 pixels, about 150 pixels. Selecting a surface peak from each cluster may comprise calculating the center of gravity of the cluster and identifying the surface peak that is closest to the calculated center of gravity. Alternatively, the surface peaks in a cluster may be merged by averaging or computing the center of gravity of the cluster, where the average or center of gravity is a cumulative surface peak. Alternatively, selecting a surface peak from each cluster may comprise comparing the pixel intensities of the surface peaks and selecting the surface peak with the highest pixel intensity. The thicker-lined circles 302 in FIG. 3B represent the selected surface peaks as a result of step 208. Next, the method 200 may comprise defining a rectangle 210 around each of the selected surface peaks. A rectangle may have a length m and a width n (m×n), where m and n may be from about 5 mm to about 25 mm, e.g., about 16 mm, about 5 mm, about 10 mm, etc., or in terms of image pixels, m and n may be from about 10 pixels to about 100 pixels, e.g., about 40 pixels, about 50 pixels, about 60 pixels, about 75 pixels, etc. A rectangle may be centered around a selected surface peak, in some instances. The rectangles may also be squares or any other shape. For example, a rectangle may be defined around a selected surface peak (x1, y1) by setting the vertices of the rectangle at a certain distance d_s away from the selected surface peak (e.g., vertex 1: (x1−d_s, y1−d_s), vertex 2: (x1+d_s, y1−d_s), vertex 3: (x1−d_s, y1+d_s), vertex 2: (x1+d_s, y1+d_s)). Distance d_s may be, for example 40 pixels to about 100 pixels, e.g., about 60 pixels, for an image size of about 400×400 pixels. If two or more rectangles overlap each other, they may be merged to form a single larger rectangle. For example, the boundaries of the single larger rectangle may be delineated by setting the coordinates for the vertices as the minimum and maximum x-coordinate and y-coordinates across both rectangles (i.e., top edge is aligned along the maximum y-value, bottom edge is aligned along the minimum y-value, left edge is aligned along the minimum x-value, right edge is aligned along the maximum x-value).

Figure 3C:
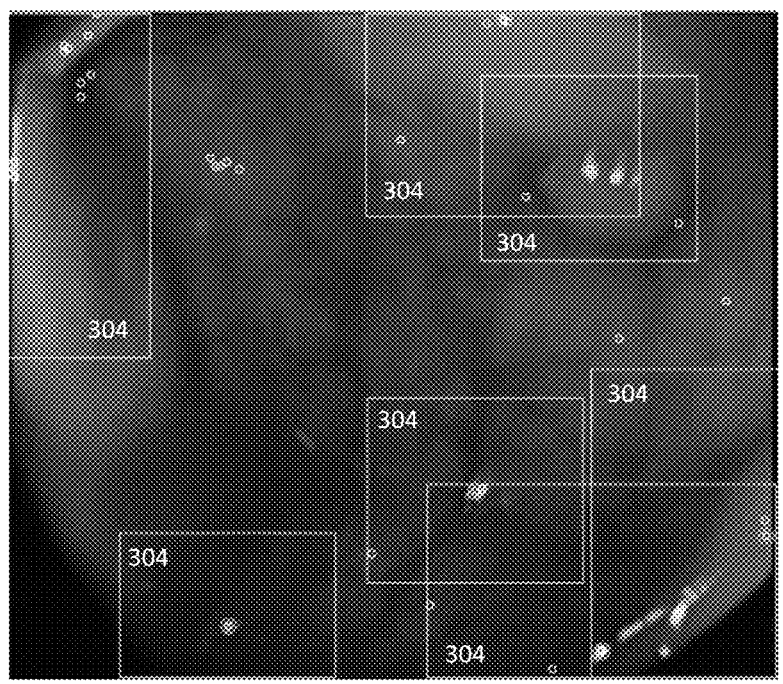

In some variations, the shape of the region may be characterized by a cluster of pixels that meet certain selection characteristics (e.g., RGB values and/or brightness values), which may or may not have a pre-defined shape. For example, in some variations, rectangles may delineate the boundaries of pixel regions that may comprise groups of pixels that have certain characteristics or features that are correlated with the presence of a polyp. Examples of image features that may be used to identify whether an image contains a polyp or not may include surface peak densities (e.g., number of surface peaks per area of colon), high-intensity pixel densities, size and shape of high-contrast edges, spatial frequency of low-contrast edges, RGB values and/or changes of RGB values across a region, etc. Pixel regions that have surface peak densities that meet or exceed a pre-determined surface peak density threshold, and/or disparate RGB values, and/or curved high-contrast edges that have a radius of curvature below a pre-determined curvature threshold (e.g., a sharply curved edge with a smaller radius of curvature) may be correlated with a polyp structure. In addition, oval-shaped and/or rounded edges (e.g., relatively high-contrast edges) that may be fully connected or partially connected, and/or a surface peak located in the vicinity of the oval-shaped and/or rounded edges (e.g., within the inner or concave portion of the rounded edges) may also be correlated with a polyp structure. In contrast, low surface peak densities, similar RGB values across the region (e.g., homogenous RGB values), and/or curved edges that have a radius of curvature above a pre-determined curvature threshold may be correlated with non-polyp structures. Low-contrast edges with high spatial frequencies may be correlated with non-polyp structures or features, such as vascular patterns on the interior surface of the colon. Regions with RGB values in the blue or purple range may be considered a polyp-like feature while regions with RGB values in the pink or red range may be considered a non-polyp feature. FIG. 3C depicts rectangles defined by step 210. In some variations, closely clustered rectangles (such as the three rectangles in the lower right quadrant of FIG. 3C) may be combined into a single, larger rectangle, as described above.

Figure 2B:
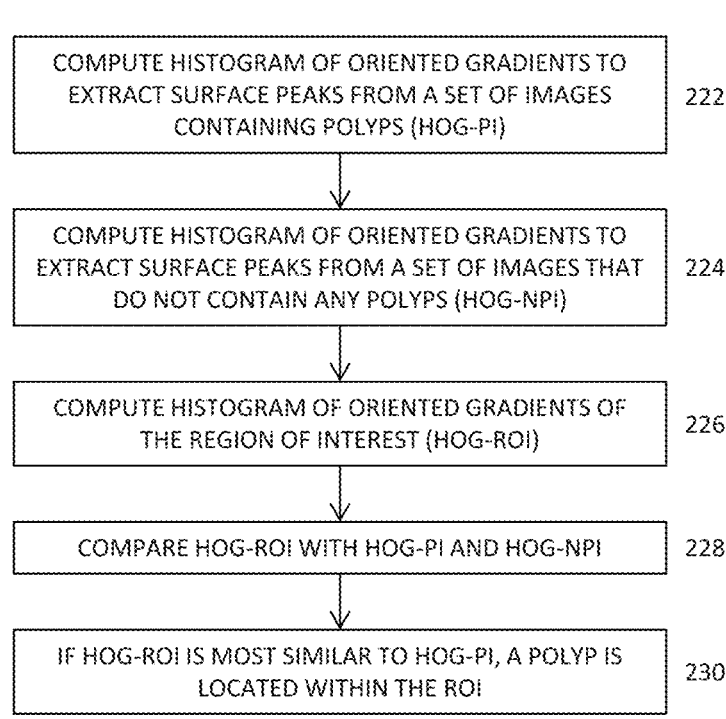
FIG. 2B is a flowchart depiction of one variation of a method for comparing image features of a region of interest with image features of polyp images and non-polyp images.
Figure 3D:
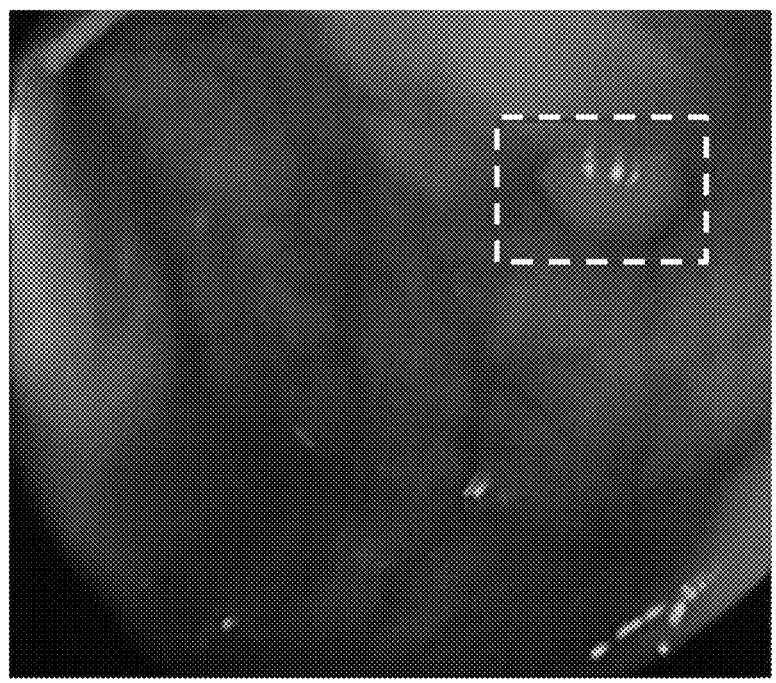

Method 200 may then comprise comparing features 212 in the enclosed region of a rectangle to a database of images with polyps and a database of images without polyps. This comparison step 212 may be carried out for each of the regions enclosed by the rectangles from step 210, and may be executed in parallel or executed sequentially. Methods of comparison may include various learning models, for example, a non-probabilistic binary linear classifier, a non-linear classifier (e.g., applying a kernel function) which may comprise regression analysis and clustering methods. Some methods may comprise applying one or more convolutional neural networks (CNNs) to identify images that have features correlated with the presence of polyps. One variation of a method 220 that may be used in step 212 of method 200 is depicted in FIG. 2B. Method 220 may comprise computing a histogram of oriented gradients 222 to extract surface peaks from a set of images containing polyps (HOG-PI), computing a histogram of oriented gradients 224 to extract surface peaks from a set of images that do not contain any polyps (HOG-NPI), computing a histogram of oriented gradients 226 of a region of interest (i.e., the region of the image enclosed in a rectangle; HOG-ROI), compare HOG-ROI with HOG-PI and HOG-NPI 228, and if HOG-ROI is most similar to HOG-PI, then a polyp is determined to be located within the ROI (step 230). In some variations, the HOG of polyp-containing images and non-polyp-containing images may be computed once at the start of a colonoscopy session and not computed or updated until the next colonoscopy session. One variation of a method for computing the histogram of oriented gradients of an image (or a region of interest within an image) may comprise dividing the image or region of interest within an image into overlapping blocks that each has a 2×2 array of cells. For example, an image having a size of 64×128 pixels may be divided into a 16×16 array of blocks, where 50% of each block overlaps with its neighboring block. Each block in the array may have 2×2 array of cells, which each cell has a size of 8×8 pixels. The HOG method may further comprise computing centered horizontal and vertical gradients, computing gradient orientation and magnitudes, and quantizing the gradient orientation into 9 angular bins (from 0 to 180) according to the computed gradient orientation. Various learning models, for instance, SVM, that compare different image feature characteristics or parameters may be used. FIG. 3D depicts the result of step 212, where a polyp is detected in one rectangle and but not the others. If any polyps were identified in one or more rectangles, method 200 comprises generating a notification 214 to inform the practitioner of the possible presence of a polyp in an image. A practitioner may optionally confirm the presence of a polyp, or instead determine that the method 200 yielded a false positive. After an imaging session (e.g., a colonoscopy session), the images that have been determined to be polyp-positive may be added to the set of images with polyps and the images that have been determined to be polyp-negative may be added to the set of images without polyps. The sets of polyp-positive and polyp-negative images may be updated periodically using newly classified images from the same or different clinic. In some variations, images that have been classified by a clinician may be collected across multiple offices, clinics and/or any network of service providers and used to update a database of polyp-positive images and polyp-negative images. In this way, the HOG-PI and HOG-NPI values or metrics can be constantly updated.

Figure 8:
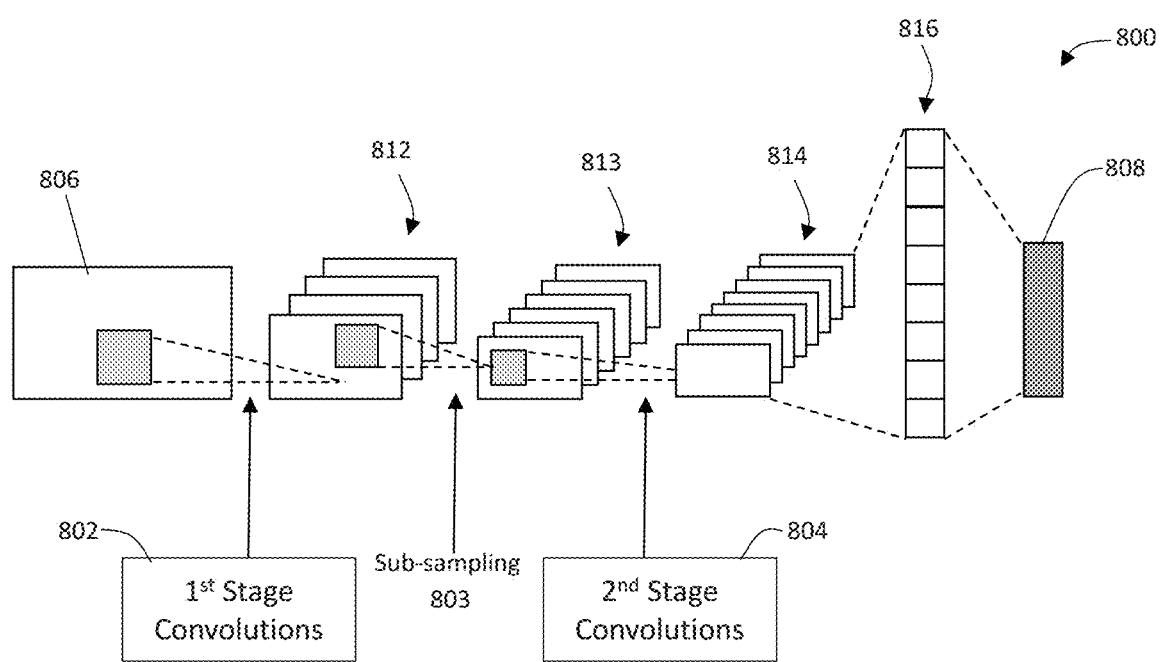
FIG. 8 depicts one variation of a convolutional neural network (CNN) that may be applied to an image for polyp detection.

Additionally or alternatively, polyp detection methods may comprise applying one or more convolutional neural networks (CNNs) to an acquired image to determine whether the image contains a polyp. One example of a CNN that may be applied to an image of the colon (either a static image or a series of images in a video, in real-time or in post-processing after a colonoscopy session) is depicted in FIG. 8. The CNN 800 may comprise a first stage of filters or convolutions 802 and a second stage of filters or convolutions 804. The image(s) acquired by an endoscope may be an input image 806 to which the CNN is applied to determine whether the image 806 contains a polyp. Applying the first stage of filters 802 to the input image 806 results in a first set of feature maps 812, subsampling 803 the first set of features maps results in a second set of feature maps 813, and applying the second stage of filters 804 results in a third set of features maps 814. Integrating the feature maps resulting from these stages of filtering or convolutions may generate a metric (e.g., a numerical score) or output 808 that represents the likelihood that the input image 806 contains a polyp. The metric or output 808 may be compared with a pre-determined or pre-selected threshold to decide whether the input image contains a polyp or not. For example, if the metric or output meets or exceeds a threshold, the input image is classified as containing a polyp (e.g., is classified as a polyp-positive image). If the metric or output is less than the threshold, the input image is classified as not containing a polyp (e.g., is classified as a polyp-negative image). Optionally, if the calculated metric is within a specified range of the threshold (e.g., within a calculation error margin), the system may prompt the clinician to direct their attention to the detected features and to confirm whether or not the feature is a polyp.

In some variations, the first stage of filters or convolutions and/or the second stage of filters or convolutions may include the method depicted in FIG. 2B. Alternatively or additionally, the first stage of filters or convolutions may select for image features that are correlated with polyps (i.e., a polyp-positive filter may select for a polyp-like feature set). For example, the first stage of filters 802 may identify regions in the input image 806 that have a HOG (i.e., HOG-ROI) that is similar to the HOG of polyp-positive image(s) (i.e., HOG-PI). Other examples of polyp-positive or polyp-like features may include oval-shaped and/or rounded edges (e.g., relatively high-contrast edges) that may be fully connected or partially connected, and/or a surface peak located in the vicinity of the oval-shaped and/or rounded edges, a high-contrast edge having a curve with a radius-of-curvature from about 2 mm to about 7 mm, and/or surface peaks identified by calculating a histogram of oriented gradients of a plurality of polyp-positive colon images (HOG-PI), etc. A first stage of filters or convolutions may identify polyp-like image features. Filters or convolutions may also eliminate image regions that have more non-polyp features than poly-like features. Examples of non-polyp features (i.e., that may be selected by a polyp-negative filter or convolution) may include diffuse structures with relatively low contrast, and/or no surface peaks, low-contrast edges with a spatial frequency that exceeds a pre-determined spatial frequency threshold (e.g., the spatial frequency of a surface of a healthy colon wall), surface peaks identified by calculating a histogram of oriented gradients of a plurality of polyp-negative colon images (HOG-NPI), etc. These features may be correlated with non-polyp structures, such as the interior surface of the colon, vascular patterns of the colon surface, and/or residual debris from an imperfect bowel preparation, etc.). Additional image features that may be correlated with non-polyp features may include filters or convolutions may comprise a low-pass filter and/or a discrete or fast Fourier transform. Spectral image data may also be used to help identify a polyp. For example, regions with RGB values in the blue or purple range may be considered a polyp-like feature while regions with RGB values in the pink or red range may be considered a non-polyp feature. In some variations, applying filters or convolutions to an image may comprise calculating a metric or numerical output that represents the frequency or incidence of a selected image feature. For example, the numerical output may indicate the absolute or relative area of the image over which the selected feature has been detected, and/or a ratio of the number of pixels (or image area) of the detected selected feature to the number of pixels (or image area) of the image where the selected feature was not detected, and/or the number of instances that the selected feature has been detected in the image, etc. In some variations, a count metric or output may comprise the number of image sub-regions that have more polyp-like features than non-polyp features. If the count metric meets or exceeds a pre-determined count threshold, the image may be classified as a polyp-positive image. Alternatively or additionally, a ratio metric or output may comprise a ratio of the number of image sub-regions that have more polyp-like features than non-polyp features to the number of image sub-regions that have fewer polyp-like features than non-polyp features. If the ratio metric meets or exceeds a pre-determined ratio threshold, the image may be classified as a polyp-positive image.

The first set of feature maps 812 may be sampled to select for pixel groups or image regions that possess the image features selected by the first stage of filters or convolutions. The second set of feature maps 813 may represent the pixel groups or image regions that have any degree of similarity with polyp-positive images, even if the degree of similarity is relatively low (e.g., the frequency or number of detected incidences of polyp-like features is similar to the frequency or number of detected incidences of non-polyp features). The second set of feature maps 813 may be a sub-sample of the first set of feature maps 812. The second set of feature maps 813 may then be filtered by a second stage of filters or convolutions 814 that may identify image regions or pixel groups that have image features that are different from polyp-negative images. Alternatively or additionally, the second stage of filters or convolutions may identify image regions or pixel groups that do not contain image features or characteristics (e.g., non-polyp features) correlated with polyp-negative images and contain image features or characteristics (e.g., polyp-like features) that are correlated with polyp-positive images. Image regions that do not have features correlated with the presence of a polyp, and/or images that have features that are correlated with non-polyp structures (e.g., colon wall or folds, vascular patterns, bowel residue) may be selected out by filters or convolutions. Filters or convolutions may also select image regions for elimination by identifying image regions that have concave curves/structure, multiple lines or curves distributed across the image, and/or web-like structures that are often associated with blood vessels or perfusion, and/or any of the previously described non-polyp image features. The selection of certain features and elimination of other features may be achieved by applying one or more of the filters or convolutions described above.

Applying the second stage of filters or convolutions 814 to the second set of feature maps 814 may result in an integrated set of maps from which the metric or output 808 may be calculated. As an example, the second stage of filters or convolutions may generate a polyp surface peak similarity metric that represents the similarity of a set of feature maps to the surface peaks of a polyp-positive image. The second stage of filters or convolutions may generate a non-polyp surface peak similarity metric that represents the similarity of a set of feature maps to the surface peaks of a polyp-negative image. In some variations, the polyp surface peak similarity metric and the non-polyp surface peak similarity metric may be compared to calculate the metric or output 808. For example, if the polyp surface peak similarity metric is greater than the non-polyp surface peak similarity metric and the difference exceeds a first pre-determined threshold, the output of the CNN may be that the image contains a polyp. If the polyp surface peak similarity metric is less than the non-polyp surface peak similarity metric, and the difference exceeds a second pre-determined threshold, the output of the CNN may be that the image does not contain a polyp. If the difference in these metrics is below any of the pre-determined thresholds, the system may generate a notification to the clinician to examine the image more closely in order to determine whether a polyp is present or not.

One or more of the steps of method 200 and method 220 may be implemented in computer-executable instructions. The processor or controller may comprise a central processing unit (CPU), one or more memories in communication with the central processing unit, and an input-output (I/O) interface that facilitates the communication between the CPU and any peripheral devices, such as the imaging devices of the endoscope system, display, remote server, keyboard, mouse, etc. Image data acquired by any of the imaging devices may be transmitted to the CPU through the I/O interface. Optionally, image data may undergo pre-processing in a video box prior to being transmitted to the CPU. In some variations, raw image data may also be transmitted to the display. Analysis of the image data to detect polyps (e.g., steps 204-212 of method 200 and steps 222-230 of method 220) may be carried out by the CPU. Raw image data, intermediate images (such as those depicted in FIGS. 3A-3D), and computer-executable instructions that correspond to the method steps depicted in FIGS. 2A and 2B may be stored in the one or memories and accessed as needed by the CPU. Any visual notifications (e.g., error messages, identification of polyps, navigational cues, etc.) may be generated by the CPU and transmitted to the display via the I/O interface. Images that have been acquired and analyzed in the course of a colonoscopy may optionally be transmitted to a remote server (e.g., cloud server) that may categorize the images as "polyp images" (e.g., polyp-positive image) or "non-polyp images" (e.g., polyp-negative image). In some variations, data relating to whether an image generated a false positive or false negative may also be transmitted to the remote server. As the database of these images increases (i.e., as more and more practitioners upload colonoscopy images to the server), the polyp identification method may become more sensitive to structures along the colon surface that may be polyps or lesions.

Images from a previous session that have been classified as polyp-positive or polyp-negative may be stored in a local and/or remote database. For example, images that have been classified locally (and optionally visually confirmed by a clinician) as a polyp-positive image or a polyp-negative image may be transmitted to a remote or cloud server. Some systems may optionally incorporate these images in one or more CNNs for polyp detection, which may facilitate and/or expedite the accurate detection of polyps. For example, images that have been classified as polyp-positive may be used to define (or refine) polyp-positive filters or convolutions in a CNN to help identify features in a newly acquired image (i.e., an input image) that are correlated with, and/or indicate the presence of, one or more polyps. Similarly, images that have been classified as polyp-negative may be used to define (or refine) polyp-negative filters or convolutions in a CNN to help identify features in a newly acquired image that are correlated with non-polyp tissue (e.g., features that indicate the absence of polyps or are indicative of colon surface folds, vascular patterns or bowl debris). For example, the surface peak features/characteristics (e.g., histogram of oriented gradients or HOGs) of polyp-positive images and/or the surface peak features/characteristics (e.g., HOGs) of polyp-negative images may be implemented in a filter or convolution stage to generate feature maps of image regions or pixel groups, as described previously. In some variations, the filter or convolutions a CNN may be updated using local image data (e.g., images acquired during colonoscopies at a single location (e.g., a single office or clinic) and/or may be updated using image data aggregated over multiple locations (e.g., a network or group of clinics or offices). Image data that is used to update CNN filters or convolutions may include full images (which may or may not be classified as polyp-positive or polyp-negative images), selected feature maps and/or extracted features, subsamples of feature maps or filtered images, and/or images or feature maps that generated by summing a plurality of images or feature maps. Image data may be uploaded to a remote server where it is stored until the next CNN update. For example, image data may be uploaded to a remote server once a day and/or at the completion of a colonoscopy session, and updates to a CNN based on newly uploaded image data may be transmitted to local CNNs once a day and/or upon user-initiated update commands.

Polyp detection methods may include multiple CNNs to identify a variety of image features or characteristics that are correlated with the presence of a polyp in an image, and/or identifying features or characteristics that are correlated with the absence of a polyp in an image. For example, a polyp detection method may comprise a first CNN that evaluates whether an image has one or more regions that have HOG profiles correlated with polyp-positive images and a second CNN that evaluates the image for one or more regions that have oval-shaped or rounded high-contrast edges (which may or may not be fully connected). Optionally, there may be a third CNN that evaluates the image for one or more regions that have diffuse, low-contrast edges, and/or web-like structures correlated with blood vessels. A polyp detection method may combine the outputs from the first CNN and the second CNN, and determine that areas where there is a surface peak located on an oval-shaped edge may have a polyp. Optionally, the method may comprise filtering out (e.g., classifying as polyp-negative) images or image regions that have been determined by the third CNN to be polyp-negative. The outputs of multiple CNNs may be weighted, for example, using coefficients that are selected at least in part based on the probability, likelihood, or correlation between that particular image feature or characteristic and the presence (or absence) of a polyp. That is, image features that are highly correlated with the presence of a polyp may be assigned a higher weight or coefficient while image features that are less correlated with the presence of a polyp may be assigned a lower weight or coefficient. Optionally, additional CNNs may be used to identify surface peak characteristics (e.g., number of peaks, distribution or density of peaks, movement of peaks across consecutive frames, etc.) that may be correlated with the presence of a polyp. Other CNNs may optionally be included that detect for any number of polyp-like features and/or non-polyp features.

Optionally, a polyp detection method may comprise a first CNN for processing images from the front-facing imaging device, and a second CNN for processing images from the side-facing imaging device(s). There may be individual, separate CNNs for each of the side-facing imaging devices. In some variations, polyp detection methods may use images only from the side-facing imaging devices while in other variations, polyp detection methods may use images from both the front-facing and side-facing imaging devices. For example, a polyp detection method may comprise applying a first CNN on images acquired by a first side-facing imaging device and applying a second CNN on images acquired by a second side-facing device. If a polyp is detected in an image from a side-facing imaging device, the clinician may be prompted to direct the colonoscope so that the detected polyp is in the field-of-view of the front-facing imaging device for closer examination and/or confirmation.

Figure 6A:
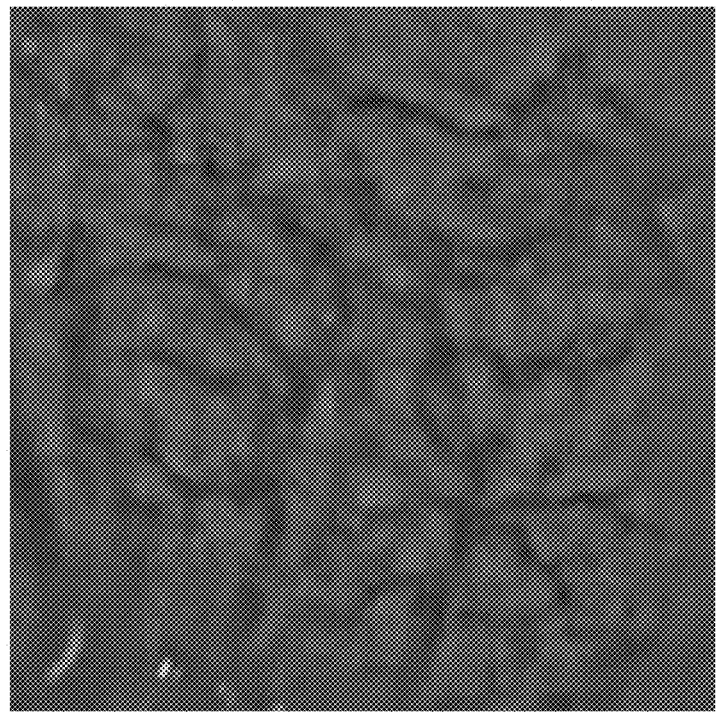
FIG. 6A is an image acquired by an endoscope depicting an example of a vascular pattern on the internal surface of a colon.
Figure 6B:
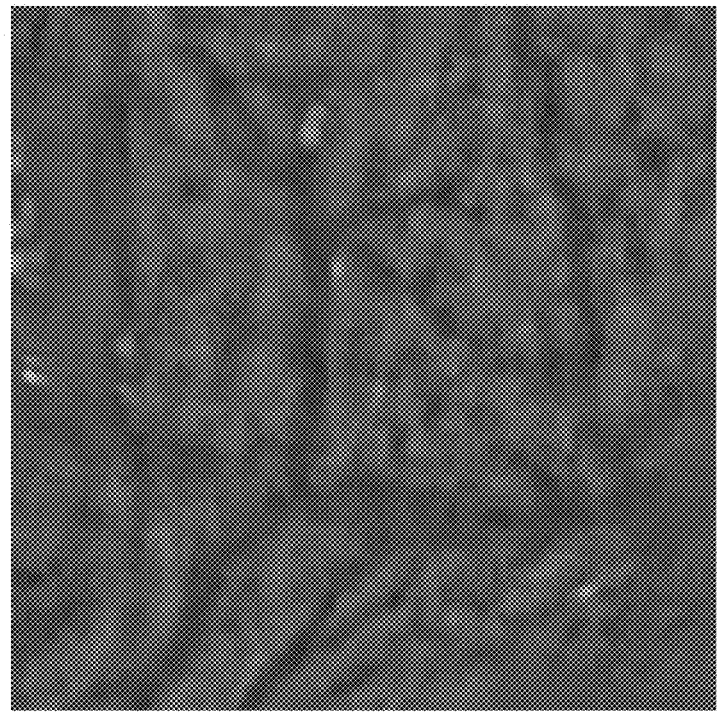
FIG. 6B is an image acquired by an endoscope depicting another example of a vascular pattern on the internal surface of a colon.

In some variations, a polyp detection method may optionally comprise identifying characteristics of the polyp and its surrounding colon surface environment and storing data pertaining to those characteristics in a memory of the processor. This may allow a practitioner to determine whether a polyp has been encountered previously, or is a newly identified polyp. Examples of polyp parameters that may be stored and used to identify a polyp may include size, shape, light reflection properties, circumferential location, longitudinal location (e.g., colon segment where the polyp is located), surface texture, coloration, etc. The location of a polyp may be computed or estimated based on image analysis of travel distance relative to an origin (e.g., motion detection) and/or anatomical structures (e.g., striated muscle patterns, characteristic curves/bends/flexures, rectum folds, vascular patterns), and reference tags selected by the practitioner. Alternatively or additionally, an accelerometer or position sensor located at or near the distal end of the elongate body of an endoscope may be used to determine the real-time location of the imaging device(s) at the time the polyp is detected. FIGS. 6A and 6B are examples of various vascular patterns in the mucosal membrane that may be used to identify the location of a polyp and/or may be used as an origin or reference point. The reference point may, for example, be stored in memory when the practitioner presses a button when the endoscope is located at a desired anatomical location. Optionally, the selected reference point may be inked. Examples of polyp environment parameters that may be stored and used to facilitate the identification of a polyp may include light reflection properties, coloration and/or textural properties of the surface surrounding the polyp, the presence or absence of other polyps or lesions, the presence or absence of certain anatomical structures, and/or vascular patterns.

Figure 7A:
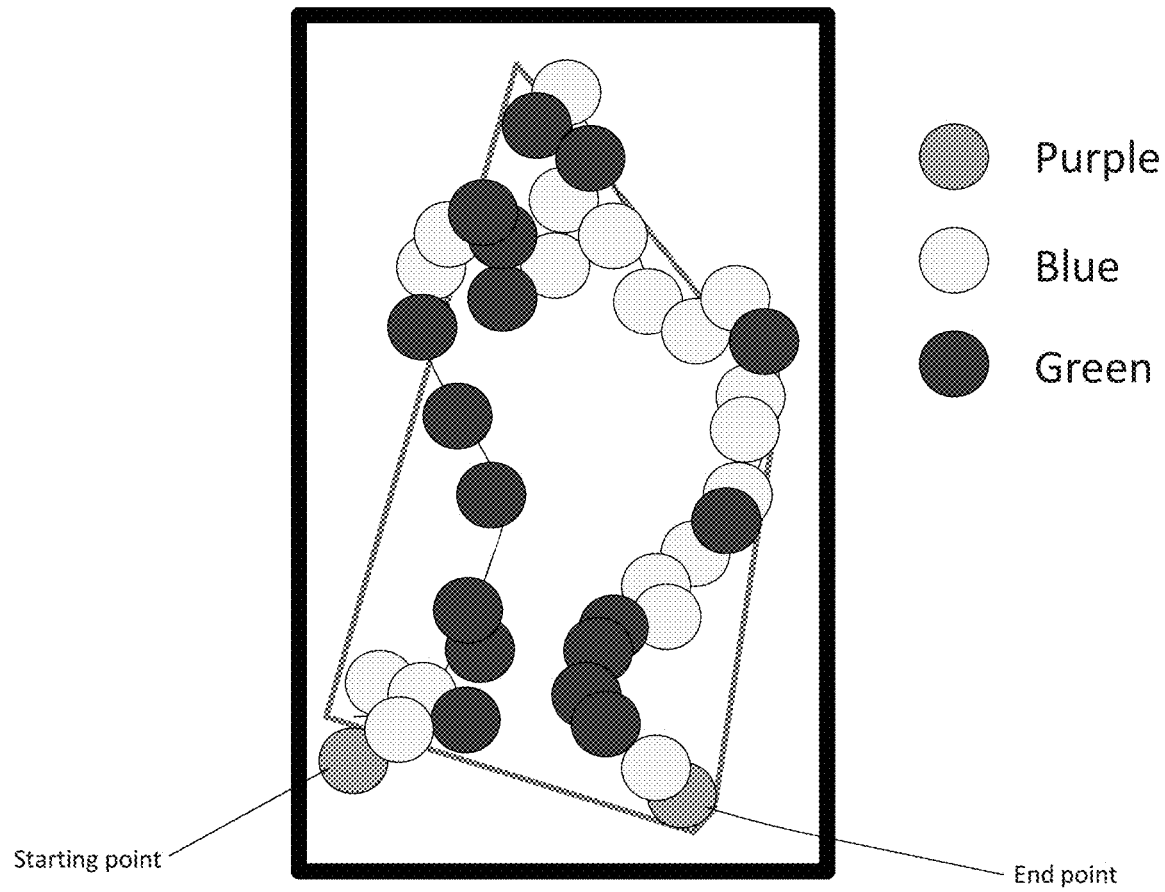
FIG. 7A depicts one variation of a plot that reflects the scan speed of an endoscope system along various segments of a colon.
Figure 7B:
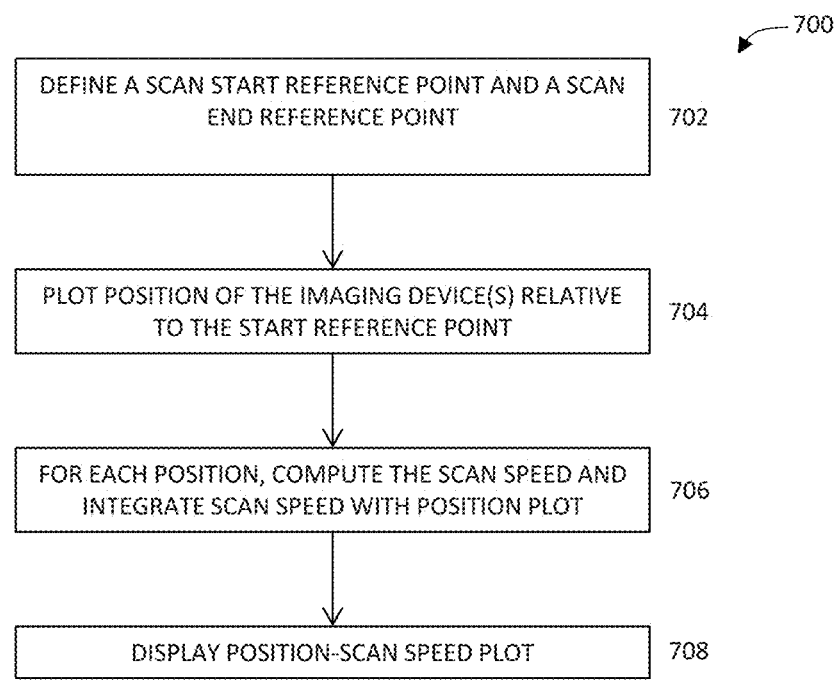
FIG. 7B is a flowchart depiction of one example of a method for generating the plot of FIG. 7A.

Position and movement data computed or estimated based on acquired images may also be used to compute the speed at which the imaging device(s) are moving at particular regions or lengths in the colon during a scan. In some variations, the position and/or orientation of the imaging device(s) in three dimensional space relative to an origin or reference point may be estimated using motion detection methods, and/or optionally, with accelerometer and/or position sensor data. Scanning speed and corresponding location/position data may be stored in a memory of the processor, and the processor may generate a plot representing the scan speed at various colon segments that is displayed to the practitioner. One example of such a plot is depicted in FIG. 7A. In some variations, scanning speeds may be represented by different colors at each location of the colon. For example, a green dot (or any desired marker or indicator) at a particular colon segment may indicate that the scanning speed was greater than a predetermined high-speed threshold, and a blue dot may indicate that the scanning speed was less than a predetermined low-speed threshold (e.g., completely stopped). In some variations, a purple colored dot may indicate segments of the colon that have been scanned more than once. Optionally a third color may be used to represent when the scan speed is within a predetermined range. One variation of a method 700 for generating the position-scan speed plot of FIG. 7A is represented in the flowchart depicted in FIG. 7B. As depicted there, method 700 may comprise defining 702 a scan start reference point and a scan end reference point. In some examples, the end reference point may be the same as the start reference point, while in other examples, the end reference point may be different from the start reference point. These reference points may be automatically assigned by the processor, which may be configured to detect when the endoscope system is inserted into the colon, and/or may be assigned as desired by the practitioner. Method 700 may further comprise plotting 704 the position of the imaging device(s) of the endoscope system related to the starting reference point during the scan. The real-time position of the imaging device(s) relative to the starting reference point may be determined using any of the methods described above, and/or optionally using data from a gyroscope and/or accelerometer located on the elongate body of the endoscope system. The position of the imaging device(s) may be represented, for example, by a dot. For example, if the imaging device(s) move to the left/right of the starting reference point, a dot is plotted to the left/right of the reference point on the plot, and if the imaging device(s) move forward/backward to the reference point, a dot is plotted forward/backward of the reference point, and so on. The method 700 may further comprise computing 706 the scan speed at the positions represented by the dots, and integrating this data with the position data. For example, the dots may be color-coded as indicated above, or the transparency or intensity of the dot color may be proportional to the scan speed, etc. The position-scan speed plot may then be displayed 708 to the practitioner. Optionally, the curvature of the colon and/or the travel trajectory of the endoscope system may be approximated by a line on the position-scan speed plot. This plot may provide feedback to the practitioner as to how long the practitioner spent examining certain segments of the colon, and may facilitate the detection of colon segments that the practitioner may have missed. The data from a position-scanning speed plot may also be used to facilitate practitioner training, for example, allowing the practitioner to determine whether they consistently miss inspecting certain areas of the colon, and/or whether they spend too much time inspecting other areas of the colon, and may also assist the practitioner in pacing the scan speed at a desired rate. The position-scanning speed plot (such as that depicted in FIG. 7A) may be generated by the processor and displayed during the scanning session (thereby providing real-time feedback to the practitioner) and/or may be generated by the processor after the conclusion of the scan. Scanning speed data (e.g., a position-scanning speed plot) may also be transmitted to a remote server.

Figure 4A:
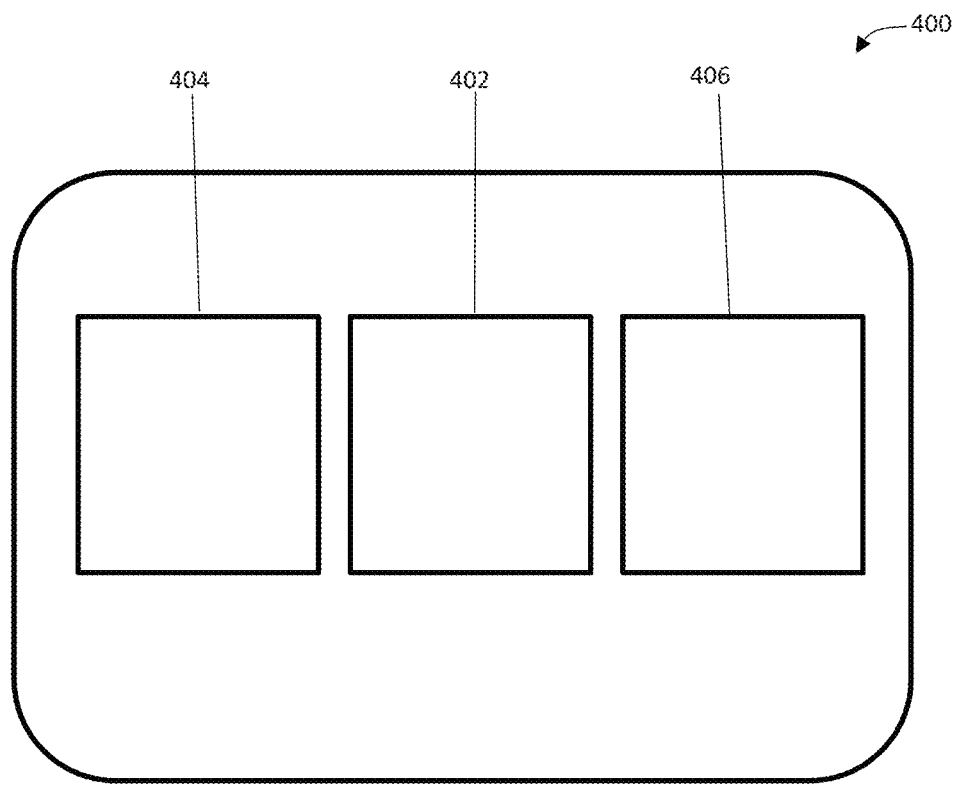
FIG. 4A is a schematic representation of one variation of a display format.
Figure 4B:
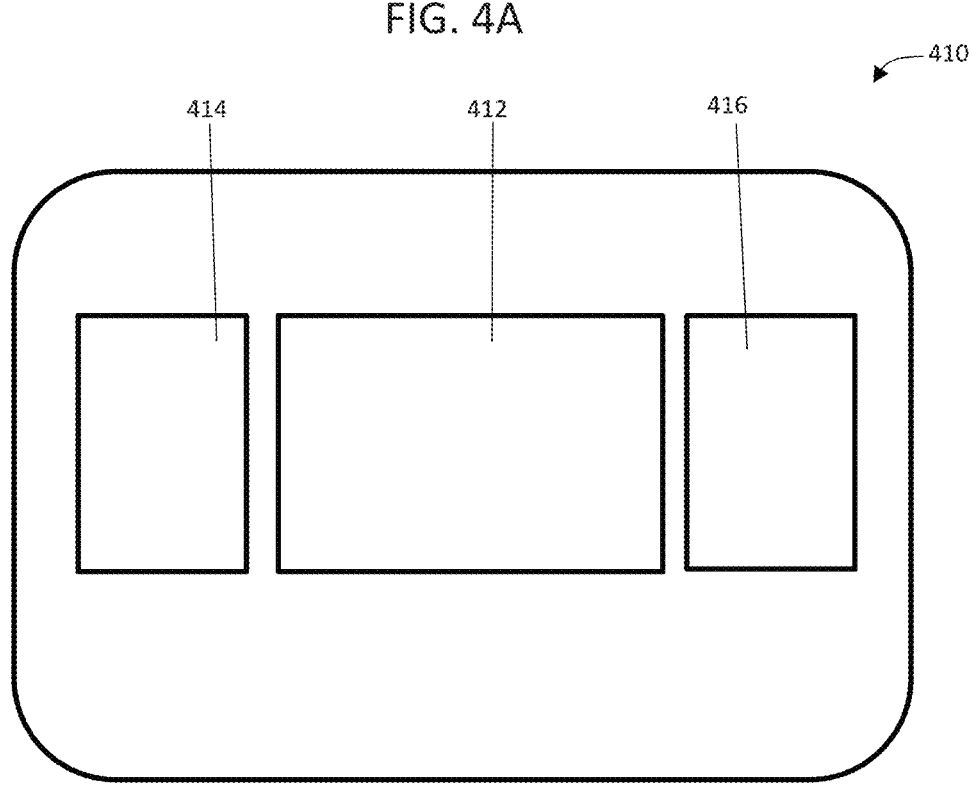
FIG. 4B is a schematic representation of another variation of a display format.
Figure 5A:
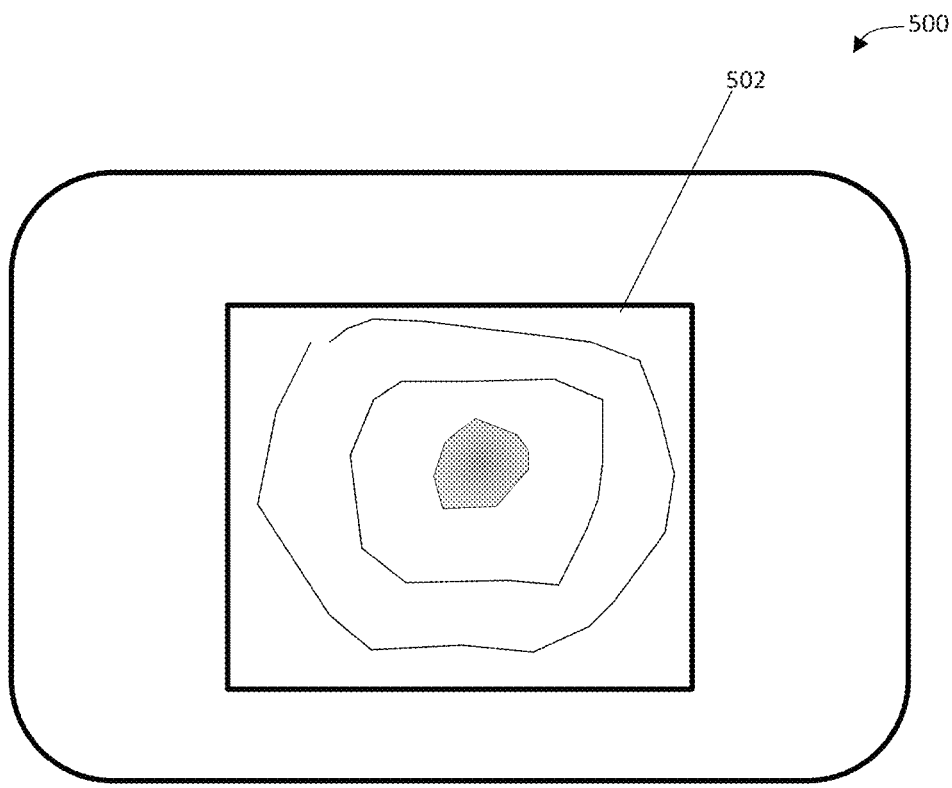
FIG. 5A is a schematic representation of one variation of a display format when a polyp has not been detected.
Figure 5B:
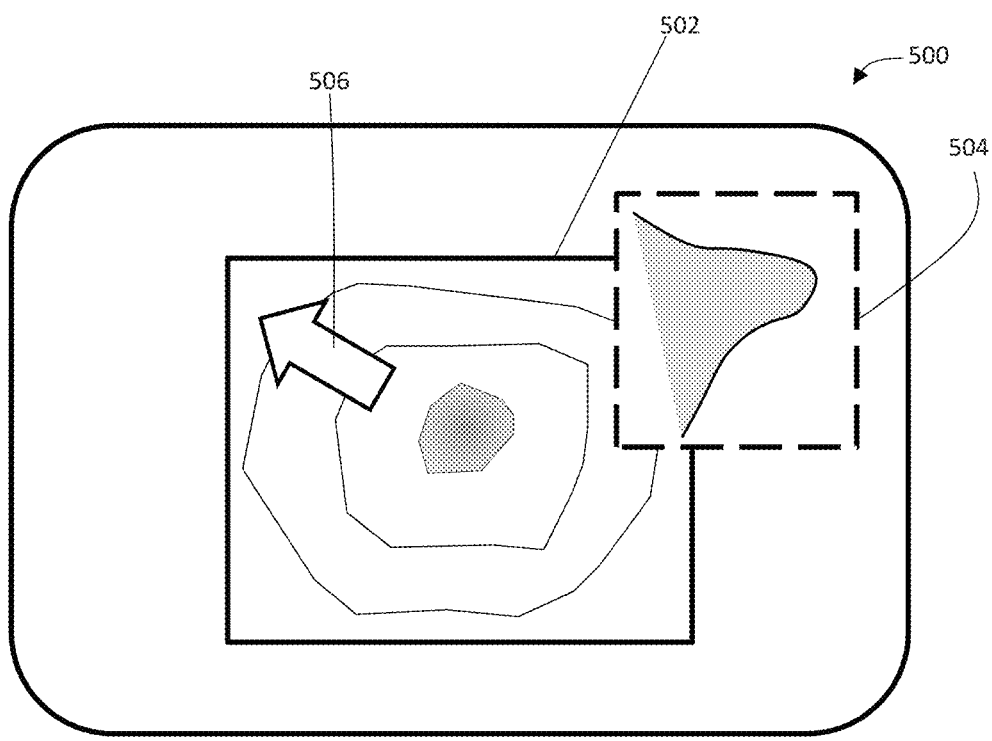
FIG. 5B is a schematic representation of the display format of FIG. 5A when a polyp has been detected.

When a polyp is detected by the processor or controller, a notification may be provided to the practitioner conducting the scan. Various types of notifications may be used to inform the practitioner of the presence and location of a polyp. FIG. 4A depicts one variation of a display 400 where a first image 402 from a front-facing imaging device is located in the center of the display with the images from the side-mounted imaging devices (e.g. first side-facing image 404 and second side-facing image 406) located around the first image 402 (i.e., on either side of the first image). The images 402, 404, and 406 may be the scaled such that they are substantially the same size. FIG. 4B depicts a variation where the image 414 from the front-facing imaging device is larger (e.g., having a greater area, and/or greater length and/or greater width) than the images 414, 416 from the side-mounted imaging devices. For the display formats depicted in FIGS. 4A and 4B, the processor may outline the edges of detected polyp in whichever image that contains the polyp. For example, if a polyp is detected in right image 406, the edge of the polyp may be highlighted or outlined in image 406. If the practitioner steers the endoscope so that the polyp is in view of the front-facing imaging device and the polyp appears on the center image 402, then the edge of the polyp may be highlighted or outlined in image 402. In some variations, movement of the endoscope with respect to the polyp may be represented by transient shadows to help cue the practitioner as to the direction of movement and/or orientation of the distal end of the endoscope. FIGS. 5A and 5B depict another variation of a display that may be included with any of the endoscope systems described herein. In this example, the images from the one or more side-mounted imaging devices are not included on the display unless a polyp is detected in one of those images. This may help to limit visual clutter for the practitioner, which may in turn help clarify the orientation of the distal end of the colonoscope with respect to the colon. While the practitioner is moving through the colon and no polyp is detected, the practitioner may have the view as depicted in FIG. 5A. The display 500 shows the image 502 as acquired from the front-facing imaging device. Although the display 500 does not depict the images acquired from the one or more side-mounted imaging devices, those devices may be continuously acquiring image data and the processor may be continuously analyzing image data from the one or more side-mounted imaging devices to detect polyps. If a polyp is detected in one of the side-mounted imaging devices, the image 504 containing the polyp 504 may appear on the display 500, and an arrow 506 may appear in the image 502 to help the practitioner navigate towards the detected polyp, as depicted in FIG. 5B. The practitioner may have the option of steering the endoscope toward the detected polyp to acquire further images to confirm that it is a true polyp or lesion, and/or to biopsy or excise the polyp.

Optionally, a processor may provide navigational guidance to a practitioner to provide advanced notice of approaching curves in the colon. This may help to reduce the likelihood of a practitioner advancing the distal end of the endoscope into the wall of the colon (which often causes discomfort or pain to the patient). In one variation, the processor may be configured to identify features in an image that indicate a change in the curvature of the colon lumen, and when a change in curvature is detected, an arrow may appear on the display that indicates the direction of the curvature change. In some variations, the processor may track the movement of the darkest region of the image, where the darkest region of the image may represent the region of the colon furthest from the endoscope. If the upcoming length of colon is relatively straight, the location of the darkest region of the image may remain in a central area of the image as the endoscope is advanced forward. If the upcoming length of colon curves, the location of the darkest region of the image may shift away from the central area of the image as the endoscope is advanced. For example, if the colon segment curves to the right, the darkest region in the image may move towards the right. If the area of the image occupied by the dark region monotonically grows, the processor may interpret such visual cue as the endoscope is moving in a trajectory that will impact or collide with the colon wall. The processor may generate a notification to prompt the practitioner to quickly steer the endoscope in the direction of the curve. The arrow may flash at a frequency that indicates the proximity of the distal end of the endoscope to the colon wall ahead of it. For example, as the distal tip nears the wall, the arrow flashing frequency may increase. Alternatively or additionally, an audible signal may be generated if the processor determines that the distal tip of the endoscope is within a predetermined distance from a colon wall. For example, the audible signal may be a tone pulsed at an initial frequency and as the distal tip nears a colon wall and is at risk of directly contacting the wall, the frequency may increase. A method for providing navigational guidance may comprise identifying the dark region of an image (e.g., lumen of the colon) from a front-facing imaging device of a colonoscope, determining whether the dark region remains in a central area of the image (or field-of-view of the front-facing imaging device) as the colonoscope is advanced, and if the dark region shifts from the central area of the image, providing an indication to the clinician to steer the colonoscope in the direction of the shift. The method may optionally comprise determining whether the area occupied by the dark region monotonically grows as the colonoscope is advanced and providing an indication to the clinician to steer the colonoscope away from the wall of the colon (e.g., steer left or right).

It should be understood that while the polyp detection methods described above are employed in the context of an endoscope or colonoscope system, these methods may also be used to analyze images collected by any imaging system suitable for scanning the internal surface of the colon. For example, polyp detection methods may be used to analyze images acquired using capsule or pill-based imaging systems, which may be ingested or otherwise inserted into the gastrointestinal tract. Examples of such systems are described in U.S. Pat. No. 7,039,453.

An endoscope system may comprise a controller in communication with the endoscope and the imaging devices mounted thereon and/or attached thereto. The controller may comprise one or more processors and one or more machine-readable memories in communication with the one or more processors. The controller may be connected to the imaging devices by wired or wireless communication channels.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like, and portable or wearable augmented reality devices that interface with an operator's environment through sensors and may use head-mounted displays for visualization and user input.

In some embodiments, a processor may be any suitable processing device configured to run and/or execute a set of instructions or code and may include one or more data processors, image processors, graphics processing units, digital signal processors, and/or central processing units. The processor may be, for example, a general purpose processor, Field Programmable Gate Array (FPGA), an Application Specific Integrated Circuit (ASIC), or the like. The processor may be configured to run and/or execute application processes and/or other modules, processes and/ or functions associated with the system and/or a network associated therewith. The underlying device technologies may be provided in a variety of component types, e.g., metal-oxide semiconductor field-effect transistor (MOS-FET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, or the like.

In some embodiments, memory may include a database and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor to execute modules, processes and/or functions associated with the system, such as one or more of the polyp detection methods described herein, images to be analyzed, and previously analyzed and/or classified image data. Alternatively or additionally, the memory may store data relating to one or more CNNs.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

A user interface may serve as a communication interface between an operator and the endoscope system. The user interface may comprise an input device and output device (e.g., touch screen and display) and be configured to receive input data and output data from one or more of the imaging devices, an input device, output device, network, database, and server. For example, images acquired by an imaging device may be received by the user interface, processed by processor and memory, and displayed by the output device (e.g., monitor display). Sensor data from one or more sensors (e.g., accelerometer, temperature sensor, position sensor, gyroscope, etc.) may be received by the user interface and output visually, audibly, and/or through haptic feedback by one or more output devices. As another example, operator control of an input device (e.g., joystick, keyboard, touch screen) may be received by the user interface and then processed by the processor and the memory for controlling the movement of the endoscope and/or operation of the one or more imaging devices.

In variations of an input device comprising at least one switch, a switch may comprise, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive operator movement data from an optical sensor and classify an operator gesture as a control signal. A microphone may receive audio and recognize an operator voice as a control signal. In variations of a system comprising a plurality of input devices, different input devices may generate different types of signals.

In variations of the input device comprising one or more buttons, button presses of varying duration may execute different functions. For example, a lumen output level of a light source may be configured to increase with a longer button press. Conversely, a shorter duration button press may correspond to a different function such as deactivating the light source.

In some variations, a system may comprise a plurality of input devices provided in separate housings, where for example a first input device may be handheld and/or portable while a second input device may be stationary. In some variations, a first input device may comprise a tablet including a touch screen display and a second input device may comprise a step switch or foot pedal. The step switch may in some variations be a confirmation switch that must be engaged at the same time as contact with the touch screen before a control signal is transmitted to the surgical system. Output of a control signal upon simultaneous engagement of a first input device and second input device may confirm that operator input to the first input device is intentional.

An output device of an endoscope system may output sensor data corresponding to a patient and/or endoscope system, and may comprise one or more of a display device, audio device, and haptic device. The output device may be coupled to a patient platform and/or disposed on a medical cart adjacent to the patient and/or operator. In other variations, the output device may be mounted to any suitable object, such as furniture (e.g., a bed rail), a wall, a ceiling, and may be self-standing.

A display device may allow an operator to view images acquired by the one or more imaging devices. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

An audio device may audibly output patient data, sensor data, system data, alarms and/or warnings. For example, the audio device may output an audible warning when the distal end of the endoscope is detected as approaching a wall of the colon. As another example, audio may be output when operator input is overridden by the system to prevent potential harm to the patient and/or endoscope system. In some variations, an audio device may comprise at least one of a speaker, piezoelectric audio device, magnetostrictive speaker, and/or digital speaker. In some variations, an operator may communicate to other users using the audio device and a communication channel. For example, the operator may form an audio communication channel (e.g., VoIP call) with a remote operator and/or observer.

A haptic device may be incorporated into one or more of the input and output devices to provide additional sensory output (e.g., force feedback) to the operator. For example, a haptic device may generate a tactile response (e.g., vibration) to confirm operator input to an input device (e.g., touch surface). As another example, haptic feedback may notify that an operator input is overridden by the surgical system to prevent potential harm to the patient and/or system.

In some embodiments, the systems, apparatuses, and methods may be in communication with other computing devices via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, apparatuses, and methods described herein may include a radiofrequency receiver, transmitter, and/or optical (e.g., infrared) receiver and transmitter to communicate with one or more devices and/or networks.

Although the foregoing variations have, for the purposes of clarity and understanding, been described in some detail by of illustration and example, it will be apparent that certain changes and modifications may be practiced, and are intended to fall within the scope of the appended claims. Additionally, it should be understood that the components and characteristics of the systems and devices described herein may be used in any combination. The description of certain elements or characteristics with respect to a specific figure are not intended to be limiting or nor should they be interpreted to suggest that the element cannot be used in combination with any of the other described elements. For all of the variations described above, the steps of the methods may not be performed sequentially. Some steps are optional such that every step of the methods may not be performed.

The invention claimed is:

1. A method for lesion detection, comprising the steps of:
   in an image of a body region acquired from an imaging module located at a distal portion of an endoscope, by processor of a computer, identifying surface peaks in the acquired image, the surface peaks identified via histograms of oriented gradients (HOG) and/or maximally stable extremal region (MSER);
   by processor of the computer, identifying regions of interest around the one or more identified surface peaks based on one or more of clustering of surface peaks, a separation distance, surface peak density, high intensity pixel densities, size and shape of high-contrast edges, spatial frequency of low-contrast edges, RGB values, and/or changes of RGB values across a region;
   by processor of the computer, within the region(s) of interest, identifying features likely to be lesions of interest by applying a convolutional neural network (CNN) designed to compare the region(s) of interest to with a plurality of images containing lesions and a plurality of images that do not contain lesions; and
   for features likely to be lesions of interest based on application of the CNN, computing an indication of the identification of the identified likelihood.

2. The method of claim 1, wherein:
identifying the surface peaks comprises computing a histogram of oriented gradients.

3. The method of claim 1, wherein:
the identifying features likely to be lesions of interest comprises identifying a curvature of a high-contrast edge.

4. The method of claim 1, wherein:
wherein the endoscope is a colonoscope, the body region is a colon of a patient, and the lesions of interest are colon polyps.

5. The method of claim 4:
wherein applying a convolutional neural network (CNN) to the region(s) of interest further comprises:
   generating a first filtered pixel region by filtering the pixel region with a first filter to identify one or more polyp-like features,
   generating a second filtered pixel region by filtering the first filtered pixel region with a second filter to identify one or more non-polyp features, and
further comprising generating a notification that a polyp has been detected based on whether a one of the region(s) of interest has been identified that has a higher incidence of polyp-like features than non-polyp features.

6. The method of claim 1:
wherein the imaging module comprises a first side-facing imaging device and a second side-facing imaging device, and
wherein the image has been acquired from a first image from the first side-facing imaging device and a second image from the second side-facing imaging device.

7. The method of claim 1, further comprising:
by processor of a computer, identifying regions from around the region(s) of interest where a ratio of the incidence of the polyp-like feature to the incidence of the non-polyp feature exceeds a pre-determined threshold.

8. The method of claim 1, wherein:
the identifying of regions of interest around the one or more identified surface peaks is based, as least in part, on surface peak density.

9. The method of claim 7, wherein:
the identifying of regions of interest around the one or more identified surface peaks is based, as least in part, on a radius of curvature of a high contrast edge.

10. The method of claim 9 wherein:
the identifying of regions of interest around the one or more identified surface peaks is based, as least in part, on a location of a pixel having a local maximum intensity relative to an inner curve of the high-contrast edge.

11. The method of claim 1, wherein:
the polyp-like feature comprises surface peaks identified by calculating a histogram of oriented gradients of a plurality of polyp-positive colon images (HOG-PI).

12. The method of claim 1, wherein:
the identifying of regions of interest around the one or more identified surface peaks is based, as least in part, on spatial frequency of low-contrast edges.

13. The method of claim 1, wherein:
the identifying of regions of interest around the one or more identified surface peaks is based, as least in part, on change of RGB values across the region(s) of interest around the one or more identified surface peaks.

14. The method of claim 1:
wherein the endoscope has multiple imaging devices, and the method further comprises identifying surface peaks in images from the multiple imaging devices via histograms of oriented gradients and applying the CNN to regions of interest identified in images from the multiple imaging devices.

15. The method of claim 1:
wherein applying a convolutional neural network (CNN) to the region(s) of interest further comprises:
generating a first filtered pixel region by filtering the pixel region with a first filter to identify one or more lesion-like features,
generating a second filtered pixel region by filtering the first filtered pixel region with a second filter to identify one or more non-lesion features, and
further comprising generating a notification that a lesion has been detected based on whether a one of the region(s) of interest has been identified that has a higher incidence of lesion-like features than non-lesion features.

16. An apparatus, comprising:
a processor, and a non-transitory memory having stored therein one or more programs programmed to cause the processor to:
in an image of a body region acquired from an imaging module located at a distal portion of an endoscope, identify surface peaks in the image, the surface peaks identified via histograms of oriented gradients (HOG) and/or maximally stable extremal region (MSER);
identify regions of interest around the one or more identified surface peaks based on one or more of clustering of surface peaks, a separation distance, surface peak density, high intensity pixel densities, size and shape of high-contrast edges, spatial frequency of low-contrast edges, RGB values, and/or changes of RGB values across a region;
within the region(s) of interest, identify features likely to be lesions of interest by applying a convolutional neural network (CNN) designed to compare the region(s) of interest to with a plurality of images containing lesions and a plurality of images that do not contain lesions; and
for features likely to be lesions of interest based on application of the CNN, compute an indication of the identification of the identified likelihood.

17. The apparatus of claim 16, wherein the programs are further programmed to:
identify the surface peaks by computing a histogram of oriented gradients.

18. The apparatus of claim 16, wherein the programs are further programmed to:
apply a convolutional neural network (CNN) to the region(s) of interest based on training of the CNN on images with lesions and images without lesions.

19. The apparatus of claim 16, wherein:
wherein the endoscope is a colonoscope, the body region is a colon of a patient, and the lesions of interest are colon polyps.

20. The apparatus of claim 16, wherein the programs are further programmed to cause the processor to:
identify features likely to be lesions of interest based at least in part on identifying a curvature of a high-contrast edge.

21. The apparatus of claim 16, wherein:
wherein the endoscope is a colonoscope, the body region is a colon of a patient, and the lesions of interest are colon polyps.

22. The apparatus of claim 16:
wherein the programs to apply a convolutional neural network (CNN) to the region(s) of interest are further programmed to cause the processor to:
generate a first filtered pixel region by filtering the pixel region with a first filter to identify one or more polyp-like features,
generate a second filtered pixel region by filtering the first filtered pixel region with a second filter to identify one or more non-polyp features, and
the programs are further programmed to cause the processor to generate a notification that a polyp has been detected based on whether a one of the region(s) of interest has been identified that has a higher incidence of polyp-like features than non-polyp features.

23. The apparatus of claim 16:
wherein the imaging module comprises a first side-facing imaging device and a second side-facing imaging device, and
wherein the image has been acquired from a first image from the first side-facing imaging device and a second image from the second side-facing imaging device.

24. The apparatus of claim 16, the programs being further programmed to cause the processor to:
by processor of a computer, to identify regions from around the region(s) of interest where a ratio of the incidence of the polyp-like feature to the incidence of the non-polyp feature exceeds a pre-determined threshold.

25. The apparatus of claim 16, wherein:
the identifying of regions of interest around the one or more identified surface peaks is based, as least in part, on surface peak density.

26. The apparatus of claim 16, wherein:
the identifying of regions of interest around the one or more identified surface peaks is based, as least in part, on a radius of curvature of a high contrast edge.

27. The apparatus of claim 16 wherein:
the identifying of regions of interest around the one or more identified surface peaks is based, as least in part, on a location of a pixel having a local maximum intensity relative to an inner curve of the high-contrast edge.

28. The apparatus of claim 16, wherein:
the polyp-like feature comprises surface peaks identified by calculating a histogram of oriented gradients of a plurality of polyp-positive colon images (HOG-PI).

29. The apparatus of claim 16, wherein:
the identifying of regions of interest around the one or more identified surface peaks is based, as least in part, on spatial frequency of low-contrast edges.

30. The apparatus of claim 16, wherein:
the identifying of regions of interest around the one or more identified surface peaks is based, as least in part, on change of RGB values across the region(s) of interest around the one or more identified surface peaks.

31. The apparatus of claim 16 :
wherein the endoscope has multiple imaging devices, and
the programs are further programmed to cause the processor to identify surface peaks in images from the multiple imaging devices via histograms of oriented gradients and apply the CNN to regions of interest identified in images from the multiple imaging devices.

32. The apparatus of claim 16:
the programs are further programmed to cause the processor to apply a convolutional neural network (CNN) to the region(s) of interest are further programmed to cause the processor to:
generate a first filtered pixel region by filtering the pixel region with a first filter to identify one or more lesion-like features,
generate a second filtered pixel region by filtering the first filtered pixel region with a second filter to identify one or more non-lesion features, and
programs are further programmed to cause the processor to generate a notification that a lesion has been detected based on whether a one of the region(s) of interest has been identified that has a higher incidence of lesion-like features than non-lesion features.

* * * * *